United States Patent
Liu et al.

(10) Patent No.: US 10,640,514 B2
(45) Date of Patent: *May 5, 2020

(54) POLYMORPH OF DPPIV INHIBITOR MALEATE AND PREPARATION METHOD THEREFOR

(71) Applicant: SHANGHAI INSTITUTE OF MATERIA MEDICA, CHINESE ACADEMY OF SCIENCES, Shanghai (CN)

(72) Inventors: Hong Liu, Shanghai (CN); Jiang Wang, Shanghai (CN); Jian Li, Shanghai (CN); Jia Li, Shanghai (CN); Jingya Li, Shanghai (CN); Hualiang Jiang, Shanghai (CN); Xiaomin Luo, Shanghai (CN); Kaixian Chen, Shanghai (CN)

(73) Assignee: Shanghai Institute of Materia Medica, Chinese Academy of Sciences, Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/087,317

(22) PCT Filed: Mar. 20, 2017

(86) PCT No.: PCT/CN2017/077278
§ 371 (c)(1),
(2) Date: Sep. 21, 2018

(87) PCT Pub. No.: WO2017/162116
PCT Pub. Date: Sep. 28, 2017

(65) Prior Publication Data
US 2019/0100529 A1    Apr. 4, 2019

(30) Foreign Application Priority Data
Mar. 22, 2016  (CN) .................... 2016 1 0165572

(51) Int. Cl.
*A61K 31/519* (2006.01)
*C07D 495/04* (2006.01)
*A61P 3/10* (2006.01)

(52) U.S. Cl.
CPC .......... *C07D 495/04* (2013.01); *A61K 31/519* (2013.01); *A61P 3/10* (2018.01); *C07B 2200/13* (2013.01)

(58) Field of Classification Search
CPC .......................... A61K 31/519; C07D 495/04
USPC ........................................ 514/260.1; 544/278
See application file for complete search history.

(56) References Cited

FOREIGN PATENT DOCUMENTS

| CN | 101817833 A | 9/2010 |
| CN | 102329325 A | 1/2012 |
| WO | 2013078765 A1 | 6/2013 |

OTHER PUBLICATIONS

Int'l Search Report dated Jun. 21, 2017 in Int'l Application No. PCT/CN2017/077278.

*Primary Examiner* — Jeffrey H Murray
(74) *Attorney, Agent, or Firm* — Panitch Schwarze Belisario & Nadel LLP

(57) ABSTRACT

The invention describes a polymorph of (R)-methyl-2-(3-aminopiperidin-1-yl)-3-(2-cyanobenzyl)-4-carbonyl-3,4-dihydrothiophene[3,2-d]pyrimidine-6-carboxylic acid maleate and a preparation method therefor. The polymorph is a crystal having high stability and low hygroscopicity, and the crystal form is selected from crystal form A, crystal form B and crystal form C. Furthermore, the crystal form has a strong in-vivo hypoglycemic activity and can be used for the preparation of a novel drug for the treatment or prevention of diabetes mellitus type H and/or complications of diabetes mellitus type H.

19 Claims, 10 Drawing Sheets

0
POLYMORPH OF DPPIV INHIBITOR MALEATE AND PREPARATION METHOD THEREFOR

CROSS-REFERENCE TO RELATED APPLICATION

This application is a Section 371 of International Application No. PCT/CN2017/077278, filed Mar. 20, 2017, which was published in the Chinese language on Sep. 28, 2017, under International Publication No. WO 2017/162116 A1, which claims priority under 35 U.S.C. § 119(b) to Chinese Application No. 201610165572.4, filed Mar. 22, 2016, the disclosures of which are incorporated herein by reference in their entirety.

TECHNICAL FIELD

The present invention relates to the field of medicinal chemistry, and in particular to a crystal form of (R)-methyl-2-(3-aminopiperidin-1-yl)-3-(2-cyanobenzyl)-4-carbonyl-3,4-dihydrothiophene[3,2-d]dipyrimidine-6-carboxylic acid maleate and a preparation method and use of the new crystal form.

BACKGROUND ART

Diabetes Mellitus (DM) is a chronic, systemic, metabolic disease caused by the long-term interaction of genetic factors and environmental factors. It is characterized by increased plasma glucose levels, and is a disease affecting normal physiological activities resulted from the metabolic disorder of sugar, fat and protein mainly caused by insufficient insulin secretion or dysfunction (insulin resistance) in the body. Complications of diabetes can be divided into acute complications and chronic complications, in which, acute complications include diabetic ketoacidosis, diabetic hyperosmolar coma, various acute infections and lactic acidosis etc. (hypoglycemia that occurs during the treatment of diabetes is also one of the most common acute complications); and chronic complications include diabetic eye disease, diabetic nephropathy, diabetic neuropathy, diabetic cardio-cerebral limb vascular disease, diabetic foot and skin diseases and the like. The main clinical manifestations of diabetes are polydipsia, polyuria, polyphagia and weight loss and the like.

Diabetes is divided into Insulin-Dependent Diabetes Mellitus (IDDM, i.e. type I diabetes) and Non insulin-Dependent Diabetes Mellitus (NIDDM, i.e. type II diabetes), in which type II diabetes is the most common, accounting for more than 90% of people with diabetes. The exact etiology and pathogenesis of type I diabetes is still not well understood, and it is caused by the combination of genetic and environmental factors, mainly due to the destruction of islet β-cells in the body, which leads to the inability to produce insulin in the body. Patients need to be injected with insulin daily to control their insulin level in blood. Type II diabetes is a type of metabolic syndrome that can not control blood glucose levels in the body. It is mainly characterized by hyperglycemia, insulin resistance and insufficient insulin secretion. The cause of type II diabetes is mainly due to insulin resistance, which makes the body unable to use insulin effectively, or the reduction in insulin secretion so that the needs of the body cannot be met. Because such patients with diabetes can secrete insulin, insulin therapy is generally not required, and blood glucose can be controlled only by dietary adjustment or oral hypoglycemic agents.

The drugs currently available for the treatment of type II diabetes mainly include insulin and its analogues, sulfonylureas, biguanides, α-glucosidase inhibitors, thiazolidinediones, Glucagon-Like peptide-1 (GLP-1) analog, dipeptidyl peptidase IV (DPP IV) inhibitor, and the like. Although existing drugs can control blood sugar levels and reduce the incidence of complications, most of them have serious side effects such as gastrointestinal toxicity, weight gain, edema, and hypoglycemia etc. Therefore, the treatment of type II diabetes is still a difficult problem. Finding and developing therapeutic drugs with novel mechanism of action and small side effects has become a hot spot to which both academic and industrial circles have paid attention and to be solved.

DPP IV inhibitors can significantly reduce blood glucose levels in the body, increase glucose tolerance, promote insulin secretion, reduce glucagon levels, delay insulin resistance and increase response level of insulin in patients with type II diabetes when blood glucose increases. Compared with existing oral diabetes drugs, DPP IV inhibitors have following characteristics: (1) DPP IV inhibitors do not require injections, and can continuously reduce glycosylated hemoglobin levels by oral administration; (2) long-term use of DPP IV inhibitors have good tolerance; (3) insulin secretion and the release of glucagon can be improved; (4) insulin sensitivity can be improved, while increasing pancreatic β cell function; (5) incidence of hypoglycemia is lower, and weight gain, nausea, vomiting and gastrointestinal dysfunction won't occur; (6) DPP IV inhibitors have synergistic effects when used in combination with other type II diabetes drugs.

(R)-methyl 2-(3-aminopiperidin-1-yl)-3-(2-cyanobenzyl)-4-carbonyl-3,4-dihydrothiophene[3,2-d]pyrimidine-6-carboxylic acid (compound of formula I) is a novel DPP IV inhibitor with strong hypoglycemic activity in vivo. However, the overall performance of (R)-methyl-2-(3-aminopiperidin-1-yl)-3-(2-cyanobenzyl)-4-carbonyl-3,4-dihydrothiophene[3,2-d]pyrimidine-6-carboxylic acid in the existing form of free base is not satisfactory.

Therefore, there is an urgent need in the art to develop a polymorph of (R)-methyl-2-(3-aminopiperidin-1-yl)-3-(2-cyanobenzyl)-4-carbonyl-3,4-dihydrothiophene[3,2-d]pyrimidine-6-carboxylic acid maleate (a compound of formula I) which is highly efficient, low toxicity and long-acting, the preparation method thereof is simple, thermal stability is good, hygroscopicity is low and the polymorph can be produced on a large scale to obtain pharmaceutically active ingredients with better performance.

SUMMARY OF THE INVENTION

The object of the present invention is to provide a polymorph of (R)-methyl-2-(3-aminopiperidin-1-yl)-3-(2-cyanobenzyl)-4-carbonyl-3,4-dihydrothiophene[3,2-d]pyrimidine-6-carboxylic acid maleate (compound of formula I) which is highly efficient, low toxicity and long-acting.

In the first aspect of the invention, a crystal form of a compound of formula I is provided, the crystal form is a crystal of high stability and low hygroscopicity, and the crystal form is selected from the group consisting of crystal form A, crystal form B and crystal form C

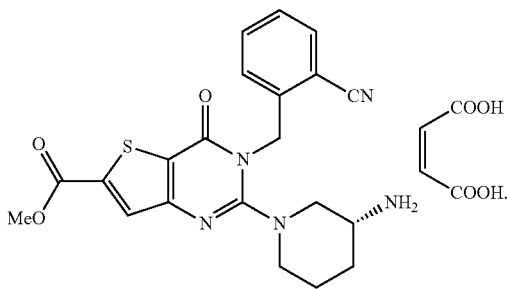

In another preferred embodiment, the "low hygroscopicity" means that the weight gain of the crystal form A, crystal form B or crystal form C is calculated to be ≤1%, after being placed in a desiccator for 24 hours at a temperature of 80° C. and a humidity of 80% and taken out.

In another preferred embodiment, the weight gain is ≤0.5%, more preferably ≤0.3%.

In another preferred embodiment, the X-ray powder diffraction pattern of the crystal form A comprises 3 or more 2θ values selected from the group consisting of: 3.72±0.2°, 7.47±0.2°, 11.44±0.2°, 12.28±0.2°, 21.59±0.2°.

In another preferred embodiment, the X-ray powder diffraction pattern of the crystal form A includes 3 or more 2θ values selected from the group consisting of: 3.72±0.2°, 7.47±0.2°, 10.74±0.2°, 11.44±0.2°, 12.28±0.2°, 14.30±0.2°, 15.20±0.2°, 17.11±0.2°, 17.32±0.2°, 18.16±0.2°, 19.22±0.2°, 21.59±0.2°, 23.15±0.2°, 25.76±0.2°, 28.02±0.2°, 32.82±0.2°.

In another preferred embodiment, the characteristic absorption peak represented by the 2θ value of the X-ray powder diffraction pattern of the crystal form A has a deviation of ±0.5, preferably a deviation of ±0.3, more preferably a deviation of ±0.1.

In another preferred embodiment, the X-ray powder diffraction pattern of the crystal form A is substantially characterized as in FIG. 1.

In another preferred embodiment, the differential scanning calorimetry analysis spectrum (DSC spectrum) of the crystal form A has a characteristic peak within the range of 118±5° C.

In another preferred embodiment, the differential scanning calorimetry analysis spectrum of the crystal form A has a characteristic absorption peak at 118.37° C.

In another preferred embodiment, the differential scanning calorimetry analysis spectrum of the crystal form A is substantially characterized as in FIG. 3.

In another preferred embodiment, the thermogravimetric analysis spectrum of the crystal form A comprises 3 or more characteristic absorption peaks selected from the group consisting of: 63±5° C., 184±5° C., 215±5° C., 287±5° C., 325±5° C.

In another preferred embodiment, the thermogravimetric analysis spectrum of the crystal form A comprises 3 or more characteristic absorption peaks selected from the group consisting of: 62.6° C., 184.3° C., 214.9° C., 286.6° C., 324.6° C.

In another preferred embodiment, the thermogravimetric analysis spectrum (TG spectrum) of the crystal form A is substantially characterized as in FIG. 2.

In another preferred embodiment, the crystal form A has a thermal weight loss of from 47 to 48% by weight at 400° C.

In another preferred embodiment, the crystal form A has a thermal weight loss of 47.97 wt % at 400° C.

In another preferred embodiment, the starting value of the endothermic transition temperature of the crystal form A is 115±2° C., preferably 115.04° C.

In another preferred embodiment, the hygroscopicity of crystal form A is ≤3%, preferably ≤1%, more preferably ≤0.5%, most preferably ≤0.3%.

In another preferred embodiment, the DVS pattern of crystal form A is substantially shown in FIG. 4.

In another preferred embodiment, the Raman spectrum of the crystal form A includes the following characteristic absorption peaks expressed by wavelength λ: 2226±2 $cm^{-1}$, 1716±2 $cm^{-1}$, 1689±2 $cm^{-1}$, 1604±2 $cm^{-1}$, 1566±2 $cm^{-1}$, 1536±2 $cm^{-1}$, 1486±2 $cm^{-1}$, 1393±2 $cm^{-1}$.

In another preferred embodiment, the Raman spectrum of the crystal form A includes the following characteristic absorption peaks expressed by wavelength λ: 2226 $cm^{-1}$, 1716 $cm^{-1}$, 1689 $cm^{-1}$, 1604 $cm^{-1}$, 1566 $cm^{-1}$, 1536 $cm^{-1}$, 1486 $cm^{-1}$, 1393 $cm^{-1}$.

In another preferred embodiment, the Raman spectrum of crystal form A is substantially shown in FIG. 5.

In another preferred embodiment, the IR pattern of the crystal form A includes the following characteristic absorption peaks expressed by wavelength λ: 3435±2 $cm^{-1}$, 2952±2 $cm^{-1}$, 2225±2 $cm^{-1}$, 1718±2 $cm^{-1}$, 1685±2 $cm^{-1}$, 1558±2 $cm^{-1}$, 1531±2 $cm^{-1}$, 1452±2 $cm^{-1}$, 1234±2 $cm^{-1}$, 1064±2 $cm^{-1}$, 862±2 $cm^{-1}$, 756±2 $cm^{-1}$.

In another preferred embodiment, the IR pattern of the crystal form A includes the following characteristic absorption peaks expressed by wavelength λ: 3435 $cm^{-1}$, 2952 $cm^{-1}$, 2225 $cm^{-1}$, 1718 $cm^{-1}$, 1685 $cm^{-1}$, 1558 $cm^{-1}$, 1531 $cm^{-1}$, 1452 $cm^{-1}$, 1234 $cm^{-1}$, 1064 $cm^{-1}$, 862 $cm^{-1}$, 756 $cm^{-1}$.

In another preferred embodiment, the IR pattern of crystal form A is substantially shown in FIG. 6.

In another preferred embodiment, the X-ray powder diffraction pattern of the crystal form B includes 3 or more 2θ values selected from the group consisting of: 5.37±0.2°, 12.01±0.2°, 14.93±0.2°, 16.04±0.2°, 20.09±0.2°.

In another preferred embodiment, the X-ray powder diffraction pattern of the crystal form B includes 3 or more 2θ values selected from the group consisting of: 5.37±0.2°, 7.85±0.2°, 11.20±0.2°, 12.01±0.2°, 14.93±0.2°, 16.04±0.2°, 20.09±0.2°, 22.10±0.2°, 22.61±0.2°, 24.19±0.2°, 30.16±0.2°, 32.12±0.2°, 32.39±0.2°.

In another preferred embodiment, the characteristic absorption peak represented by the 2θ value of the X-ray powder diffraction pattern of the crystal form B has a deviation of ±0.5, preferably a deviation of ±0.3, more preferably a deviation of ±0.1.

In another preferred embodiment, the X-ray powder diffraction pattern of the crystal form B is substantially characterized as in FIG. 7.

In another preferred embodiment, the differential scanning calorimetry analysis spectrum (DSC spectrum) of the crystal form B has a characteristic peak within the range of 137±5° C.

In another preferred embodiment, the differential scanning calorimetry analysis spectrum (DSC spectrum) of the crystal form B has a characteristic peak at 136.77° C.

In another preferred embodiment, the differential scanning calorimetry analysis spectrum of the crystal form B is substantially characterized as in FIG. 9.

In another preferred embodiment, the starting value of the endothermic transition temperature of the crystal form B is 127±2° C.

In another preferred embodiment, the starting value of the endothermic transition temperature of the crystal form B is 127.14° C.

In another preferred embodiment, the thermogravimetric analysis pattern of the crystal form B comprises 3 or more characteristic absorption peaks selected from the group consisting of: 119±5° C., 202±5° C., 284±5° C., 318±5° C.

In another preferred embodiment, the thermogravimetric analysis pattern of the crystal form B comprises 3 or more characteristic absorption peaks selected from the group consisting of: 118.7° C., 202.5° C., 283.7° C., 317.9° C.

In another preferred embodiment, the thermogravimetric analysis pattern of the crystal form B is substantially characterized as in FIG. 8.

In another preferred embodiment, the thermal weight loss of crystal form B is from 51 to 52% by weight at 400° C.

In another preferred embodiment, the thermal weight loss of crystal form B is 51.38 wt % at 400° C.

In another preferred embodiment, the hygroscopicity of crystal form B is ≤3%, preferably ≤1%, more preferably ≤0.5%, most preferably ≤0.3%.

In another preferred embodiment, the DVS pattern of crystal form B is substantially shown in FIG. 10.

In another preferred embodiment, the Raman spectrum of the crystal form B includes the following characteristic absorption peaks expressed by wavelength λ: 2234±2 $cm^{-1}$, 1718±2 $cm^{-1}$, 1693±2 $cm^{-1}$, 1607±2 $cm^{-1}$, 1565±2 $cm^{-1}$, 1536±2 $cm^{-1}$, 1476±2 $cm^{-1}$, 1386±2 $cm^{-1}$, 1349±2 $cm^{-1}$, 1216±2 $cm^{-1}$, 1174±2 $cm^{-1}$, 1047±2 $cm^{-1}$, 813±2 $cm^{-1}$, 730±2 $cm^{-1}$, 690±2 $cm^{-1}$, 641±2 $cm^{-1}$.

In another preferred embodiment, the Raman spectrum of the crystal form B includes the following characteristic absorption peaks expressed by wavelength λ: 2234 $cm^{-1}$, 1718 $cm^{-1}$, 1693 $cm^{-1}$, 1607 $cm^{-1}$, 1565 $cm^{-1}$, 1536 $cm^{-1}$, 1476 $cm^{-1}$, 1386, 1349 $cm^{-1}$, 1216 $cm^{-1}$, 1174 $cm^{-1}$, 1047 $cm^{-1}$, 813 $cm^{-1}$, 730 $cm^{-1}$, 690 $cm^{-1}$, 641 $cm^{-1}$.

In another preferred embodiment, the Raman spectrum of the crystal form B is substantially shown in FIG. 11.

In another preferred embodiment, the IR pattern of the crystal form B includes the following characteristic absorption peaks expressed by wavelength λ: 3404±2 $cm^{-1}$, 2954±2 $cm^{-1}$, 2222±2 $cm^{-1}$, 1718±2 $cm^{-1}$, 1678±2 $cm^{-1}$, 1558±2 $cm^{-1}$, 1531±2 $cm^{-1}$, 1369±2 $cm^{-1}$, 1290±2 $cm^{-1}$, 1219±2 $cm^{-1}$, 1063±2 $cm^{-1}$, 862±2 $cm^{-1}$, 775±2 $cm^{-1}$.

In another preferred embodiment, the IR pattern of the crystal form B includes the following characteristic absorption peaks expressed by wavelength λ: 3404 $cm^{-1}$, 2954 $cm^{-1}$, 2222 $cm^{-1}$, 1718 $cm^{-1}$, 1678 $cm^{-1}$, 1558 $cm^{-1}$, 1531 $cm^{-1}$, 1369 $cm^{-1}$, 1290 $cm^{-1}$, 1219 $cm^{-1}$, 1063 $cm^{-1}$, 862 $cm^{-1}$, 775 $cm^{-1}$.

In another preferred embodiment, the IR pattern of the crystal form B is substantially shown in FIG. 12.

In another preferred embodiment, the X-ray powder diffraction pattern of the crystal form C includes 3 or more 2θ values selected from the group consisting of: 6.63±0.2°, 11.16±0.2°, 17.06±0.2°, 19.46±0.2°, 20.84±0.2°, 25.74±0.2°.

In another preferred embodiment, the X-ray powder diffraction pattern of the crystal form C includes 3 or more 2θ values selected from the group consisting of: 6.63±0.2°, 8.67±0.2°, 11.16±0.2°, 11.64±0.2°, 15.24±0.2°, 16.43±0.2°, 17.06±0.2°, 17.41±0.2°, 18.00±0.2°, 18.61±0.2°, 18.90±0.2°, 19.46±0.2°, 19.96±0.2°, 20.84±0.2°, 21.35±0.2°, 22.81±0.2°, 23.11±0.2°, 23.59±0.2°, 24.7±0.2°, 25.18±0.2°, 25.74±0.2°, 27.62±0.2°, 28.32±0.2°, 31.17±0.2°.

In another preferred embodiment, the X-ray powder diffraction pattern of the crystal form C is substantially characterized as in FIG. 13.

In another preferred embodiment, the characteristic absorption peak represented by the 2θ value of the X-ray powder diffraction pattern of the crystal form C has a deviation of ±0.5, preferably a deviation of ±0.3, more preferably a deviation of ±0.1.

In another preferred embodiment, the differential scanning calorimetry analysis spectrum (DSC spectrum) of the crystal form C has a characteristic peak within the range of 161±5° C.

In another preferred embodiment, the DSC pattern of the crystal form C has a characteristic absorption peak at 160.90° C.

In another preferred embodiment, the starting value of the endothermic transition temperature of the crystal form C is 147±2° C.

In another preferred embodiment, the starting value of the endothermic transition temperature of the crystal form C is 147.02° C.

In another preferred embodiment, the differential scanning calorimetry analysis spectrum of the crystal form C is substantially characterized as in FIG. 15.

In another preferred embodiment, the thermogravimetric analysis spectrum of the crystal form C comprises a characteristic absorption peak selected from the group consisting of: 183±5° C., 212±5° C., 289±5° C.

In another preferred embodiment, the thermogravimetric analysis spectrum of the crystal form C comprises a characteristic absorption peak selected from the group consisting of: 183.3° C., 212.4° C., 288.8° C.

In another preferred embodiment, the thermogravimetric analysis spectrum of the crystal form C is substantially characterized as in FIG. 14.

In another preferred embodiment, the thermal weight loss of crystal form C is from 46 to 47% by weight at 400° C.

In another preferred embodiment, the thermal weight loss of crystal form C is of 46.30 wt % at 400° C.

In another preferred embodiment, the hygroscopicity of crystal form C is ≤3%, preferably ≤1%, more preferably ≤0.5%, most preferably ≤0.3%.

In another preferred embodiment, the DVS pattern of crystal form C is substantially shown in FIG. 16.

In another preferred embodiment, the Raman spectrum of the crystal form C includes the following characteristic absorption peaks expressed by the wavelength λ: 3383±2 $cm^{-1}$, 3378±2 $cm^{-1}$, 3370±2 $cm^{-1}$, 3288±2 $cm^{-1}$, 3163±2 $cm^{-1}$, 2963±2 $cm^{-1}$, 2230±2 $cm^{-1}$, 1719±2 $cm^{-1}$, 1558±2 $cm^{-1}$, 1478±2 $cm^{-1}$, 662±2 $cm^{-1}$.

In another preferred embodiment, the Raman spectrum of the crystal form C includes the following characteristic absorption peaks expressed by the wavelength λ: 3383 $cm^{-1}$, 3378 $cm^{-1}$, 3370 $cm^{-1}$, 3288 $cm^{-1}$, 3163 $cm^{-1}$, 2963 $cm^{-1}$, 2230 $cm^{-1}$, 1719 $cm^{-1}$, 1558 $cm^{-1}$, 1478 $cm^{-1}$, 662 $cm^{-1}$.

In another preferred embodiment, the Raman spectrum of crystal form C is substantially shown in FIG. 17.

In another preferred embodiment, the IR pattern of the crystal form C includes the following characteristic absorption peaks expressed by wavelength λ: 3428±2 $cm^{-1}$, 2936±2 $cm^{-1}$, 1640±2 $cm^{-1}$, 1514±2 $cm^{-1}$, 1463±2 $cm^{-1}$, 1418±2 $cm^{-1}$, 1385±2 $cm^{-1}$, 1272±2 $cm^{-1}$, 1136±2 $cm^{-1}$, 1022±2 $cm^{-1}$, 874±2 $cm^{-1}$, 766±2 $cm^{-1}$, 599±2 $cm^{-1}$.

In another preferred embodiment, the IR pattern of the crystal form C includes the following characteristic absorption peaks expressed by wavelength λ: 3428 $cm^{-1}$, 2936 cm$^{-1}$, 1640 cm$^{-1}$, 1514 cm$^{-1}$, 1463 cm$^{-1}$, 1418 cm$^{-1}$, 1385 cm$^{-1}$, 1272 cm$^{-1}$, 1136 cm$^{-1}$, 1022 cm$^{-1}$, 874 cm$^{-1}$, 766 cm$^{-1}$, 599 cm$^{-1}$.

In another preferred embodiment, the IR pattern of crystal form C is substantially shown in FIG. 18.

In the second aspect of the invention, a method for preparing the crystal form A according to the first aspect of the invention is provided, comprising the steps of:

(1) providing a first solution comprising a first solvent and a compound of formula I, the weight to volume ratio of the compound of formula I to the first solvent is from 0.1 g/L to 100 g/L (preferably 1 g/L to 90 g/L, more preferably 10 g/L to 60 g/L, most preferably 15 g/L to 40 g/L);

(2) mixing a second solvent with the first solution, and crystallizing at 0 to 50° C. to obtain crystal form A.

In another preferred embodiment, the concentration of the compound of formula I is 0.1 g/L-saturated concentration in the first solution.

In another preferred embodiment, the first solvent is selected from the group consisting of C1-C4 alcohol, C2-C8 ketones (preferably C3-C5 ketones), C1-C10 esters (preferably C1-C7 ester, more preferably C1-C5 ester), a halogenated C1-C6 alkane, water, or a combination thereof.

In another preferred embodiment, the second solvent is selected from the group consisting of C1-C10 ethers (preferably C1-C8 ethers, more preferably C1-C6 ethers), C2-C15 alkane (preferably C3-C10 alkane, more preferably C4-C8 alkane), tetrahydrofuran, 1,4-dioxane, or a combination thereof.

In another preferred embodiment, the C2-C8 ketones are selected from the group consisting of acetone, methyl ethyl ketone, isobutanol butanone, or a combination thereof.

In another preferred embodiment, the C1-C10 esters are selected from the group consisting of methyl formate, ethyl acetate, isobutyl formate, or a combination thereof.

In another preferred embodiment, the halogenated C1-C6 alkane is selected from the group consisting of dichloromethane, trichloromethane, or a combination thereof, preferably dichloromethane.

In another preferred embodiment, the C1-C10 esters are selected from the group consisting of petroleum ether, tert-butyl methyl ether, ethyl ether, isopropyl ether, diethyl ether, or a combination thereof.

In another preferred embodiment, the C2-C15 alkane is selected from the group consisting of n-pentane, n-hexane, n-heptane, or a combination thereof.

In another preferred embodiment, the compound of formula I is in an amorphous form.

In another preferred embodiment, after step (2), the method further comprises the following steps of: (3) filtering and/or drying the crystal form A obtained in step (2).

In another preferred embodiment, in step (3), the drying temperature is 10 to 70° C., preferably 20 to 80° C., more preferably 25 to 40° C.

In another preferred embodiment, in step (3), the drying pressure is 0 to 20 KPa, preferably 0 to 10 KPa, more preferably 5 to 10 KPa.

In another preferred embodiment, in step (3), the drying time is 5 to 150 hours, preferably 30 to 100 hours, more preferably 60 to 80 hours.

In another preferred embodiment, the yield of the crystal form A is from 50% to 99%, preferably from 75% to 99%, more preferably from 85% to 99%.

In another preferred embodiment, the concentration of the compound of formula I is from 0.1 g/L to 1000 g/L in the first solution.

In another preferred embodiment, the concentration of the compound of formula I is >1000 g/L in the first solution.

In another preferred embodiment, in step (2), the crystallization is carried out at 0 to 50° C., preferably 0 to 40° C., more preferably 20 to 30° C.

In another preferred embodiment, in step (2), the crystallization is performed under stirring.

In the third aspect of the invention, a method for preparing the crystal form B according to the first aspect of the invention is provided, comprising the steps of:

(1) providing a first solution comprising a first solvent and a compound of formula I, the weight to volume ratio of the compound of formula I to the first solvent is from 0.1 g/L to 100 g/L, preferably 1 g/L to 900 g/L, more preferably 10 g/L to 600 g/L, most preferably 50 g/L to 400 g/L;

(2) mixing a second solvent with the first solution, and crystallizing at 5 to 80° C. to obtain crystal form B.

In another preferred embodiment, the first solvent is selected from the group consisting of C1-C10 esters (preferably C1-C7 ester, more preferably C1-C5 ester), C5-C10 aromatic hydrocarbon (preferably C5-C6 aromatic hydrocarbon), C1-C10 ethers (preferably C1-C8 ether, more preferably C1-C6 ether), halogenated C1-C6 alkane, or a combination thereof.

In another preferred embodiment, the C1-C10 esters are selected from the group consisting of methyl formate, ethyl acetate, isobutyl formate, or a combination thereof.

In another preferred embodiment, the C5-C10 aromatic hydrocarbon is selected from the group consisting of benzene, toluene, furan, thiophene, naphthalene, or a combination thereof.

In another preferred embodiment, the C1-C10 ethers are selected from the group consisting of petroleum ether, tert-butyl methyl ether, ethyl ether, isopropyl ether, diethyl ether, or a combination thereof.

In another preferred embodiment, the halogenated C1-C6 alkane is dichloromethane, trichloromethane, or a combination thereof, preferably dichloromethane.

In another preferred embodiment, the compound of formula I is in an amorphous form.

In another preferred embodiment, the second solvent is selected from the group consisting of C2-C15 alkane (preferably C3-C10 alkane, more preferably C4-C8 alkane), tetrahydrofuran, 1,4-dioxane, or a combination thereof.

In another preferred embodiment, the C2-C15 alkane is selected from the group consisting of n-pentane, n-hexane, n-heptane, or a combination thereof.

In another preferred embodiment, after step (2), the following step is further comprised:

(3) filtering and/or drying the crystal form B obtained in step (2).

In another preferred embodiment, the drying temperature is from 10 to 70° C., preferably from 20 to 80° C., more preferably from 25 to 40° C.

In another preferred embodiment, pressure for the drying is from 0 to 20 kPa, preferably from 0 to 10 kPa, more preferably from 5 to 10 kPa.

In another preferred embodiment, time for the drying is from 5 to 150 hours, preferably from 30 to 100 hours, more preferably from 60 to 80 hours.

In another preferred embodiment, the yield of the crystal form B is from 50% to 99%, preferably from 75% to 99%, more preferably from 85% to 99%.

In another preferred embodiment, the concentration of the compound of formula I is from 0.1 g/L to 1000 g/L in the first solution.

In another preferred embodiment, the concentration of the compound of formula I is >1000 g/L in the first solution.

In another preferred embodiment, the crystallization is carried out at 0-50° C.

In another preferred embodiment, the crystallization is carried out at 0-40° C., preferably at 20-30° C., preferably at room temperature.

In another preferred embodiment, the crystallization is carried out with stirring.

In the fourth aspect of the invention, a method for preparing the crystal form C according to the first aspect of the invention is provided, comprising the steps of:

(1) providing a first solution comprising a first solvent and a compound of formula I, the weight to volume ratio of the compound of formula I to the first solvent is from 0.1 g/L to 100 g/L, preferably 1 g/L to 900 g/L, more preferably 10 g/L to 600 g/L, most preferably 50 g/L to 400 g/L;

(2) mixing a second solvent with the first solution, and crystallizing at 5 to 80° C. to obtain crystal form C.

In another preferred embodiment, the first solvent is selected from the group consisting of C1-C10 nitriles (preferably C1-C8 nitriles, more preferably C1-C5 nitriles), C2-C8 ketones (preferably C3-05 ketones), C1-C10 esters (preferably C1-C7 esters, more preferably C1-C5 esters), halogenated C1-C6 alkane, or a combination thereof.

In another preferred embodiment, the second solvent is selected from the group consisting of C2-C15 alkane (preferably C3-C10 alkane, more preferably C4-C8 alkane), C1-C10 ethers (preferably C1-C8 ethers, more preferably C1-C6 ethers), tetrahydrofuran, 1,4-dioxane, or a combination thereof.

In another preferred embodiment, the C2-C15 alkane is selected from the group consisting of n-pentane, n-hexane, n-heptane, or a combination thereof.

In another preferred embodiment, the C1-C10 nitriles are selected from the group consisting of formonitrile, acetonitrile, n-propionitrile, isopropionitrile, or a combination thereof.

In another preferred embodiment, the C2-C8 ketones are selected from the group consisting of acetone, methyl ethyl ketone, isobutanol butanone, or a combination thereof.

In another preferred embodiment, the C1-C10 esters are selected from the group consisting of methyl formate, ethyl acetate, isobutyl formate, or a combination thereof.

In another preferred embodiment, the C1-C10 ethers are selected from the group consisting of petroleum ether, tert-butyl methyl ether, ethyl ether, isopropyl ether, diethyl ether, or a combination thereof.

In another preferred embodiment, the halogenated C1-C6 alkane is dichloromethane, trichloromethane, or a combination thereof, preferably dichloromethane.

In another preferred embodiment, the compound of formula I is in an amorphous form.

In another preferred embodiment, after step (2), the following step is further comprised:

(3) filtering and/or drying the crystal form C obtained in step (2).

In another preferred embodiment, the drying temperature is from 10 to 70° C., preferably from 20 to 80° C., more preferably from 25 to 40° C.

In another preferred embodiment, pressure for the drying is from 0 to 20 kPa, preferably from 0 to 10 kPa, more preferably from 5 to 10 kPa.

In another preferred embodiment, time for the drying is from 5 to 150 hours, preferably from 30 to 100 hours, more preferably from 60 to 80 hours.

In another preferred embodiment, the yield of the crystal form C is from 50% to 99%, preferably from 75% to 99%, more preferably from 85% to 99%.

In another preferred embodiment, the concentration of the compound of formula I is from 0.1 g/L to 1000 g/L in the first solution.

In another preferred embodiment, the concentration of the compound of formula I is >1000 g/L in the first solution.

In another preferred embodiment, the crystallization is carried out at 0-50° C.

In another preferred embodiment, the crystallization is carried out at 0-40° C., preferably at 20-30° C., more preferably at room temperature.

In another preferred embodiment, the crystallization is carried out with stirring.

In the fifth aspect of the invention, a pharmaceutical composition is provided, and the composition comprises:

(a) the crystal form A, B or C according to the first aspect of the invention, and (b) a pharmaceutically acceptable carrier.

In another preferred embodiment, the pharmaceutically acceptable carrier is selected from the group consisting of a filler, disintegrant, binder, lubricant, or a combination thereof.

In another preferred embodiment, the filler is selected from the group consisting of starch, lactose, microcrystalline cellulose, dextrin, mannitol, magnesium oxide, calcium sulfate, or a combination thereof.

In another preferred embodiment, the disintegrant is selected from the group consisting of carboxymethylcellulose and a salt thereof, crosslinked carboxymethylcellulose and a salt thereof, crosslinked povidone, sodium carboxymethyl starch, low substituted hydroxypropylcellulose, or a combination thereof.

In another preferred embodiment, the binder is selected from the group consisting of povidone, hydroxypropylmethylcellulose, starch pulp, or a combination thereof.

In another preferred embodiment, the lubricant is selected from the group consisting of magnesium stearate, calcium stearate, or a combination thereof.

In the sixth aspect of the invention, a use of the crystal form according to the first aspect of the invention or the pharmaceutical composition according to the fifth aspect of the invention is provided, for the preparation of a medicament for prevention and/or treatment of type II diabetes and/or complications of type II diabetes.

In another preferred embodiment, the complications of type II diabetes mellitus are selected from the group consisting of coronary artery disease, stroke, hypertension, nephropathy, peripheral vascular disease, neurological disease, and retinopathy.

In the seventh aspect of the invention, a method for treating or preventing type II diabetes and/or complications of type II diabetes is provided, comprising administering to the patient a therapeutically effective amount of the crystal form according to the first aspect of the invention or the pharmaceutical composition according to the fifth aspect of the invention.

It should be understood that in the present invention, any of the technical features specifically described above and below (such as in the Examples) can be combined with each other, thereby constituting new or preferred technical solutions which will not redundantly be described one by one herein.

DETAILED DESCRIPTION OF INVENTION

Figure 1:
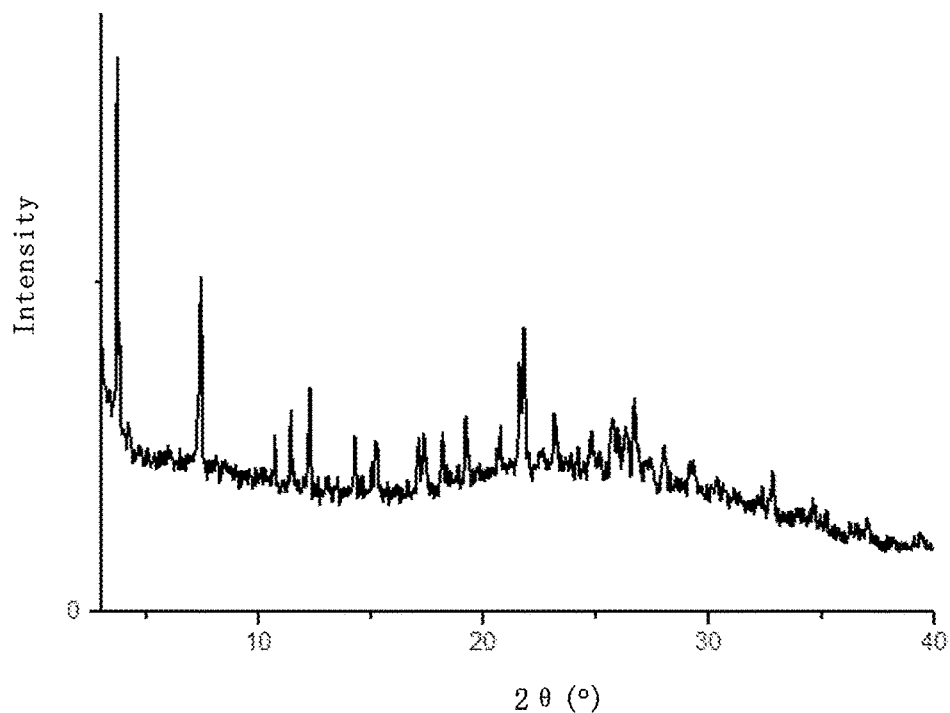
FIG. 1 is an XRD pattern of the crystal form A of a crystal of Example 1 of the present invention.

Through extensive and intensive research, the inventors have unexpectedly discovered a polymorph of (R)-methyl-2-(3-aminopiperidin-1-yl)-3-(2-cyanobenzyl)-4-carbonyl-3,4-dihydrothiophene[3,2-d]pyrimidine-6-carboxylic acid crystal maleate with better pharmaceutical properties, i.e. crystal form A, B and C. They all have good thermal stability and non-hygroscopicity, and the preparation process is simple and efficient, and the repeatability is good, and large-scale industrial production can be realized. On above basis, the present invention has been completed.

Terms

Unless otherwise defined, all technical and scientific terms used herein have the same meaning as commonly understood by one of ordinary skill in the art to which this invention belongs.

As used herein, when used in reference to a particular recited value, the term "about" means that the value can vary by no more than 1% from the recited value. For example, as used herein, the expression "about 100" includes all values between 99 and 101 (e.g., 99.1, 99.2, 99.3, 99.4, etc.).

As used herein, the terms "contains" or "includes (comprises)" may be open ended, semi-close ended and close ended. In other words, the terms also include "consisting essentially of" or "consisting of".

Compound of Formula I

The compound of formula I according to the invention is (R)-methyl-2-(3-aminopiperidin-1-yl)-3-(2-cyanobenzyl)-4-carbonyl-3,4-dihydrothiophene[3,2-d]pyrimidine-6-carbon acid.

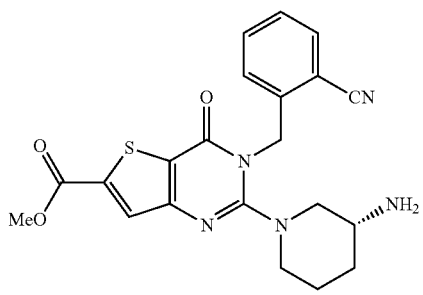

(R)-methyl-2-(3-aminopiperidin-1-yl)-3-(2-cyanobenzyl)-4-carbonyl-3,4-dihydrothiophene[3,2-d]pyrimidine-6-carboxylic acid (Formula I) is a novel DPP IV selective, reversible competitive inhibitor with strong hypoglycemic activity in vivo. Its inhibitory activity is up to nanomolar level, and its DPP IV inhibitory activity and selectivity in vitro are superior to the marketed drugs sitagliptin and vildagliptin.

In animals, the compound of formula I is effective in inhibiting DPP IV activity in normal mouse and rat plasma, and its DPP IV inhibitory activity is superior to the marketed drug alogliptin. The compound of formula I can increase oral glucose tolerance in normal ICR mice in dose-dependent manner, and onset dose thereof is only 0.1 mg/kg, and effect thereof is superior to that of alogliptin. When the compound is chronicly administered to ob/ob mice, it can effectively reduce fasting blood glucose of ob/ob mice, which is superior to positive control drug alogliptin. When the compound is chronicly administrated to gene-deficient db/db mice, it can reduce its fasting blood glucose, which is comparable to positive control drug alogliptin.

Pharmacokinetics and safety studies have shown that the compound of formula I have good pharmacokinetic properties and safety in rats and dogs, and its half-life and $AUC_{0-t}$ are superior to those of the marketed drug alogliptin in rats and dogs. The compound is safe and the acute toxicity test of ICR mice shows that no animal dies in the 300 mg/kg administration group. The acute toxicity test of Beagle dogs shows that there is no animal death in the 1 g/kg administration group. Subacute toxicity test in Rat shows that no obvious toxicity is found in orally administrated 150 mg/kg group.

Summarizing research results of pharmacodynamics evaluation in vitro, pharmacological evaluation in vivo, pharmacokinetic studies and safety evaluation etc., hypoglycemic effect of the compound in vivo is better than that of currently clinically used DPPIV inhibitors.

Polymorph

Drug Polymorphism refers to two or more different crystalline states of a drug. For solid chemical drugs, due to their different molecular arrangement and symmetry laws, one drug can form a variety of different crystalline solid matter states.

Amorphous (R)-methyl-2-(3-aminopiperidin-1-yl)-3-(2-cyanobenzyl)-4-carbonyl-3,4-dihydrothiophene[3,2-d]pyrimidine-6-carboxylic acid powder was prepared by the preparation method described in CN201210262331.3. $^1$H NMR (CDCl$_3$): δ7.76 (s, 1H), 7.610 (d, 1H), 7.493 (t, 1H), 7.320 (t, 1H), 7.180 (d, 1H), 5.500 (quartet, 2H), 3.895 (s, 3H), 3.680 (d, 2H), 3.355 (m, 1H), 3.010 (m, 2H), 2.150 (m, 1H), 1.894 (m, 2H), 1.644 (m, 1H); LC-MS m/z 424.1 [M+H]$^+$.

As used herein, "crystal form A", "crystal form A of (R)-methyl-2-(3-aminopiperidin-1-yl)-3-(2-cyanobenzyl)-4-carbonyl-3,4-dihydrothiophene[3,2-d]pyrimidine-6-carboxylic acid maleate", "the crystal form A of the compound of formula I" are used interchangeably. "Crystal form. B", "crystal form B of (R)-methyl-2-(3-aminopiperidin-1-yl)-3-(2-cyanobenzyl)-4-carbonyl-3,4-dihydrothiophene[3,2-d]pyrimidine-6-carboxylic acid maleate", "the crystal form B of the compound of formula I" are used interchangeably. "Crystal form C", "crystal form C of (R)-methyl-2-(3-aminopiperidin-1-yl)-3-(2-cyanobenzyl)-4-carbonyl-3,4-dihydrothiophene[3,2-d]pyrimidine-6-carboxylic acid maleate", "the crystal form C of the compound of formula I" are used interchangeably.

Crystal Form A

The X-ray powder diffraction pattern of the crystal form A includes 3 or more 2θ values selected from the group consisting of: 3.72±0.2°, 7.47±0.2°, 11.44±0.2°, 12.28±0.2°, 21.59±0.2°.

In another preferred embodiment, the X-ray powder diffraction pattern of the crystal form A includes 3 or more 2θ values selected from the group consisting of: 3.72±0.2°, 7.47±0.2°, 10.74±0.2°, 11.44±0.2°, 12.28±0.2°, 14.30±0.2°, 15.20±0.2°, 17.11±0.2°, 17.32±0.2°, 18.16±0.2°, 19.22±0.2°, 21.59±0.2°, 23.15±0.2°, 25.76±0.2°, 28.02±0.2°, 32.82±0.2°.

In another preferred embodiment, the X-ray powder diffraction pattern of the crystal form A is substantially characterized in FIG. 1.

Crystal Form B

In another preferred embodiment, the X-ray powder diffraction pattern of the crystal form B includes 3 or more 2θ values selected from the group consisting of: 5.37±0.2°, 12.01±0.2°, 14.93±0.2°, 16.04±0.2°, 20.09±0.2°.

In another preferred embodiment, the X-ray powder diffraction pattern of the crystal form B includes 3 or more 2θ values selected from the group consisting of: 5.37±0.2°, 7.85±0.2°, 11.20±0.2°, 12.01±0.2°, 14.93±0.2°, 16.04±0.2°, 20.09±0.2°, 22.10±0.2°, 22.61±0.2°, 24.19±0.2°, 30.16±0.2°, 32.12±0.2°, 32.39±0.2°.

Figure 7:
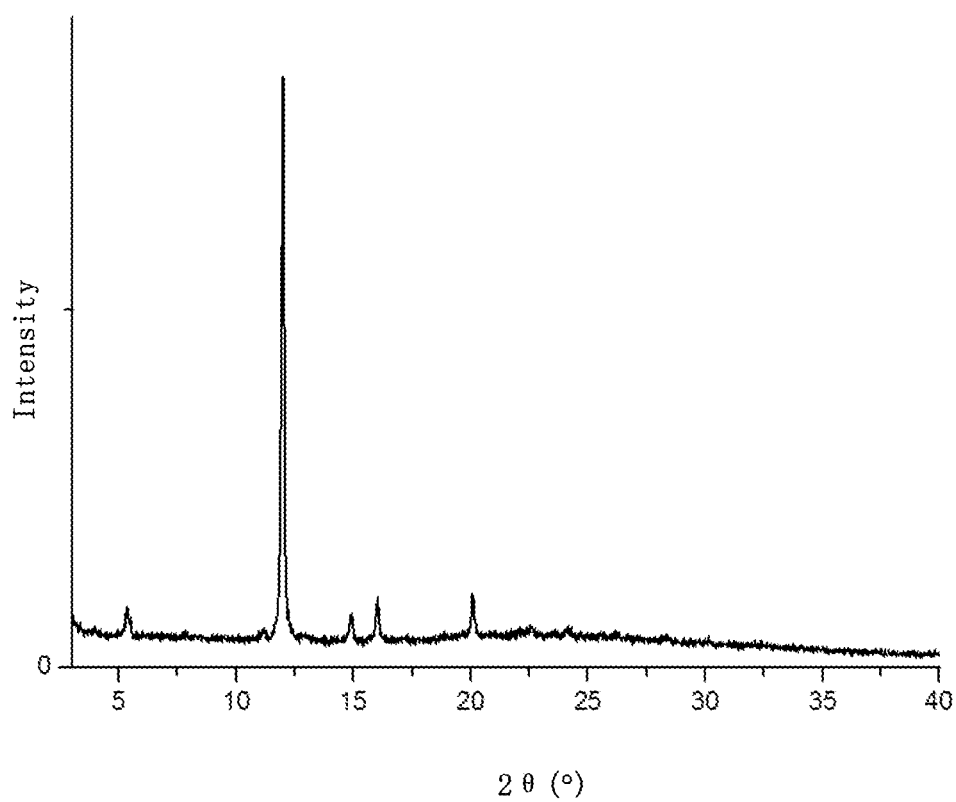
FIG. 7 is an XRD pattern of the crystal form B of a crystal of Example 4 of the present invention.

In another preferred embodiment, the X-ray powder diffraction pattern of the crystal form B is substantially characterized in FIG. 7.

Crystal Form C

In another preferred embodiment, the X-ray powder diffraction pattern of the crystal form C includes 3 or more 2θ values selected from the group consisting of: 6.63±0.2°, 11.16±0.2°, 17.06±0.2°, 19.46±0.2°, 20.84±0.2°, 25.74±0.2°.

In another preferred embodiment, the X-ray powder diffraction pattern of the crystal form C includes 3 or more 2θ values selected from the group consisting of: 6.63±0.2°, 8.67±0.2°, 11.16±0.2°, 11.64±0.2°, 15.24±0.2°, 16.43±0.2°, 17.06±0.2°, 17.41±0.2°, 18.00±0.2°, 18.61±0.2°, 18.90±0.2°, 19.46±0.2°, 19.96±0.2°, 20.84±0.2°, 21.35±0.2°, 22.81±0.2°, 23.11±0.2°, 23.59±0.2°, 24.7±0.2°, 25.18±0.2°, 25.74±0.2°, 27.62±0.2°, 28.32±0.2°, 31.17±0.2°.

Figure 13:
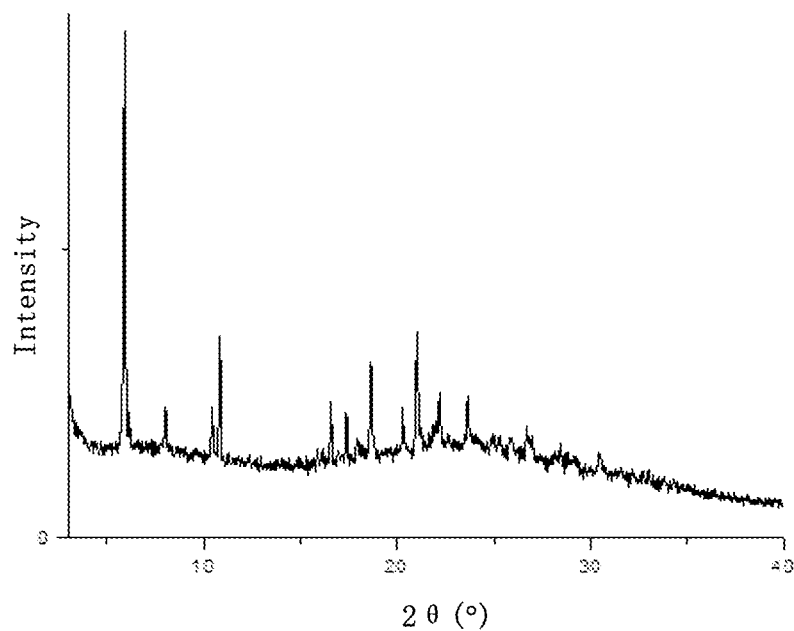
FIG. 13 is an XRD pattern of the crystal form C of a crystal of Example 7 of the present invention.

In another preferred embodiment, the X-ray powder diffraction pattern of the crystal form C is substantially characterized in FIG. 13.

Preparation Method

The invention also provides a method for the preparation of the crystal forms.

The preparation method for crystal form A according to the present invention comprises the following steps:

(1) providing a first solution comprising a first solvent and a compound of formula I, the weight to volume ratio of the compound of formula I to the first solvent is from 0.1 g/L to 100 g/L (preferably 1 g/L to 90 g/L, more preferably 10 g/L to 60 g/L, most preferably 15 g/L to 40 g/L);

(2) mixing a second solvent with the first solution, and crystallizing at 0 to 50° C. to obtain crystal form A.

In another preferred embodiment, the concentration of the compound of formula. I is 0.1 g/L-saturated concentration in the first solution.

In another preferred embodiment, the first solvent is selected from the group consisting of C1-C4 alcohol, C2-C8 ketones (preferably C3-C5 ketones), C1-C10 esters (preferably C1-C7 ester, more preferably C1-C5 ester), a halogenated C1-C6 alkane, water, or a combination thereof.

In another preferred embodiment, the second solvent is selected from the group consisting of C1-C10 ethers (preferably C1-C8 ethers, more preferably C1-C6 ethers), C2-C15 alkane (preferably C3-C10 alkane, more preferably C4-C8 alkane), tetrahydrofuran, 1,4-dioxane, or a combination thereof.

In another preferred embodiment, the C2-C8 ketones are selected from the group consisting of acetone, methyl ethyl ketone, isobutanol butanone, or a combination thereof.

In another preferred embodiment, the C1-C10 esters are selected from the group consisting of methyl formate, ethyl acetate, isobutyl formate, or a combination thereof.

In another preferred embodiment, the halogenated C1-C6 alkane is selected from the group consisting of dichloromethane, trichloromethane, or a combination thereof, preferably dichloromethane.

In another preferred embodiment, the C1-C10 esters are selected from the group consisting of petroleum ether, tert-butyl methyl ether, ethyl ether, isopropyl ether, diethyl ether, or a combination thereof.

In another preferred embodiment, the C2-C15 alkane is selected from the group consisting of n-pentane, n-hexane, n-heptane, or a combination thereof.

In another preferred embodiment, the compound of formula I is in an amorphous form.

In another preferred embodiment, after step (2), the method further comprises the following steps of: (3) filtering and/or drying the crystal form A obtained in step (2).

In another preferred embodiment, in step (3), the drying temperature is 10 to 70° C., preferably 20 to 80° C., more preferably 25 to 40° C.

In another preferred embodiment, in step (3), the drying pressure is 0 to 20 KPa, preferably 0 to 10 KPa, more preferably 5 to 10 KPa.

In another preferred embodiment, in step (3), the drying time is 5 to 150 hours, preferably 30 to 100 hours, more preferably 60 to 80 hours.

In another preferred embodiment, the yield of the crystal form A is from 50% to 99%, preferably from 75% to 99%, more preferably from 85% to 99%.

In another preferred embodiment, the concentration of the compound of formula I is from 0.1 g/L to 1000 g/L in the first solution.

In another preferred embodiment, the concentration of the compound of formula I is >1000 g/L in the first solution.

In another preferred embodiment, in step (2), the crystallization is carried out at 0 to 50° C., preferably 0 to 40° C., more preferably 20 to 30° C.

In another preferred embodiment, in step (2), the crystallization is performed with stirring.

The preparation method of the crystal form B according to the present invention, the preparation method comprises the following steps:

(1) providing a first solution comprising a first solvent and a compound of formula I, the weight to volume ratio of the compound of formula I to the first solvent is from 0.1 g/L to 100 g/L, preferably 1 g/L to 900 g/L, more preferably 10 g/L to 600 g/L, most preferably 50 g/L to 400 g/L;

(2) mixing a second solvent with the first solution, and crystallizing at 5 to 80° C. to obtain crystal form B.

The preparation method of the crystal form C of the present invention, the preparation method comprises the following steps:

(1) providing a first solution comprising a first solvent and a compound of formula I, the weight to volume ratio of the compound of formula I to the first solvent is from 0.1 g/L to 100 g/L, preferably 1 g/L to 900 g/L, more preferably 10 g/L to 600 g/L, most preferably 50 g/L to 400 g/L;

(2) mixing a second solvent with the first solution, and crystallizing at 5 to 80° C. to obtain crystal form C.

Pharmaceutical Composition and Application

The invention also provides a pharmaceutical composition comprising an active ingredient in a safe and effective amount, and a pharmaceutically acceptable carrier.

The "active ingredient" as used in the present invention means the crystal form A, B, or C of the present invention.

The "active ingredient" and pharmaceutical composition of the present invention are used for the preparation of a medicament for preventing and/or treating type II diabetes and/or complications of type II diabetes.

In another preferred embodiment, the complications of type II diabetes mellitus are selected from the group consisting of coronary artery disease, stroke, hypertension, nephropathy, peripheral vascular disease, neurological disease, and retinopathy.

It should be understood that in the present invention, the pharmaceutically acceptable carrier is not particularly limited and may be selected from conventional materials in the art, or obtained by a conventional method, or commercially available.

Representatively, the pharmaceutically acceptable carrier includes, but is not limited to, a filler, a disintegrant, a binder, a lubricant, or a combination thereof.

Typically, the filler includes (but not limited to) starch, lactose, microcrystalline cellulose, dextrin, mannitol, magnesium oxide, calcium sulfate, or a combination thereof.

Typically, the disintegrant includes (but not limited to) carboxymethylcellulose and a salt thereof, crosslinked carboxymethylcellulose and a salt thereof, crosslinked povidone, sodium carboxymethyl starch, low substituted hydroxypropylcellulose, or a combination thereof.

Typically, the binder includes (but not limited to) povidone, hydroxypropylmethylcellulose, starch pulp, or a combination thereof.

Typically, the lubricant includes (but not limited to) magnesium stearate, calcium stearate, or a combination thereof.

"Safe and effective amount" refers to: the amount of active ingredient is sufficient to significantly improve the condition, but will not have serious side effects. In general, the pharmaceutical composition contain from 1 to 2000 mg of active ingredient per dose, more preferably from 10 to 200 mg of active ingredient per dose. Preferably, the "one dose" is one tablet.

"Pharmaceutically acceptable carrier" means one or more compatible solid or liquid fillers or gelatinous materials which are suitable for human use and should be of sufficient purity and sufficiently low toxicity. "Compatibility" means that each component in the composition can be admixed with the compounds of the present invention and with each other without significantly reducing the efficacy of the compounds. Some examples of pharmaceutically acceptable carriers include cellulose and the derivatives thereof (such as sodium carboxymethyl cellulose, sodium ethyl cellulose, cellulose acetate, etc.), gelatin, talc, solid lubricants (such as stearic acid, magnesium stearate), calcium sulfate, vegetable oils (such as soybean oil, sesame oil, peanut oil, olive oil, etc.), polyols (such as propylene glycol, glycerol, mannitol, sorbitol, etc.), emulsifiers (such as Tween®), wetting agent (such as sodium dodecyl sulfate), coloring agents, flavoring agents, stabilizers, antioxidants, preservatives, pyrogen-free water, etc.

The administration mode of the compound or the pharmaceutical composition of the present invention is not particularly limited. The administration mode of the active ingredient or the pharmaceutical composition of the present invention is not particularly limited, and representative administration modes include, but are not limited to, oral, intratumoral, rectal, parenteral (intravenous, intramuscular or subcutaneous) and the like. The compounds of the invention may be administered alone or in combination with other pharmaceutically acceptable compounds. The same or similar administration modes of conventional (R)-methyl-2-(3-aminopiperidin-1-yl)-3-(2-cyanobenzyl)-4-carbonyl-3,4-dihydrothiophene[3, 2-d]pyrimidine-6-carboxylic acid can be selected, including (but not limited to) oral, transdermal, intravenous, intramuscular, topical route, and the like.

Solid dosage forms for oral administration include capsules, tablets, pills, powders and granules.

In these solid dosage forms, the active ingredient is mixed with at least one conventional inert excipient (or carrier), such as sodium citrate or dicalcium phosphate, or mixed with any of the following components: (a) fillers or compatibilizer, for example, starch, lactose, sucrose, glucose, mannitol and silicic acid; (b) binders, for example, hydroxymethyl cellulose, alginate, gelatin, polyvinylpyrrolidone, sucrose and arabic gum; (c) humectants, such as, glycerol; (d) disintegrating agents such as agar, calcium carbonate, potato starch or tapioca starch, alginic acid, certain composite silicates, and sodium carbonate; (e) dissolution-retarding agents, such as paraffin; (f) absorption accelerators, for example, quaternary ammonium compounds; (g) wetting agents, such as cetyl alcohol and glyceryl monostearate; (h) adsorbents, for example, kaolin; and (i) lubricants such as talc, calcium stearate, magnesium stearate, solid polyethylene glycol, sodium lauryl sulfate, or the mixture thereof. In capsules, tablets and pills, the dosage forms may also contain buffering agents.

The solid dosage forms can also be prepared with coatings and shell materials, such as casings and other materials known in the art. They may contain opacifying agents and the release of the active ingredient in such compositions may be released in a portion of the digestive tract in a delayed manner. Examples of embedding components that can be employed are polymeric materials and waxy materials.

Liquid dosage forms for oral administration include pharmaceutically acceptable emulsions, solutions, suspensions, syrups or tinctures. In addition to the active ingredient, the liquid dosage form may contain any conventional inert diluent known in the art such as water or other solvents, solubilizers and emulsifiers, for example, ethanol, isopropanol, ethyl carbonate, ethyl acetate, propylene glycol, 1,3-butanediol, dimethyl formamide, as well as oil, in particular, cottonseed oil, peanut oil, corn germ oil, olive oil, castor oil and sesame oil, or the mixture thereof etc. In addition to these inert diluents, the compositions may contain adjuvants such as wetting agents, emulsifying and suspending agents, sweetening agents, flavoring agents and spices.

In addition to the active ingredient, the suspension may contain suspending agent, for example, ethoxylated isooctadecanol, polyoxyethylene sorbitol and dehydrated sorbitan ester, microcrystalline cellulose, aluminum methoxide and agar, or the mixture thereof etc.

The compositions for parenteral injection may comprise physiologically acceptable sterile aqueous or anhydrous solutions, dispersions, suspensions or emulsions, and sterile powders which can be re-dissolved into sterile injectable solutions or dispersions. Suitable aqueous and non-aqueous carriers, diluents, solvents or excipients include water, ethanol, polyols and any suitable mixtures thereof.

When a pharmaceutical composition is used, a safe and effective amount of a compound of the invention is administered to a mammal (e.g., a human) in need of treatment wherein the dosage is a pharmaceutically acceptable effective dosage which varies depending on the age, sex, ethnicity, condition of the patient. For a person weighing 60 kg, the daily dose is usually from 1 to 2000 mg, preferably from 20 to 500 mg. Of course, specific doses should also consider factors such as the administration route, the health of the patient, etc., which are within the skill of the skilled physician.

Use

Also provided in the present invention is a use of the crystal form A, crystal form B and crystal form C of (R)-methyl-2-(3-aminopiperidin-1-yl)-3-(2-cyanobenzyl)-4-carbonyl-3,4-dihydrothiophene[3,2-d]pyrimidine-6-carboxylic acid maleate or the pharmaceutical composition, for the preparation of medicaments for the prevention and/or treatment of type II diabetes and/or complications of type II diabetes.

Typically, the complications of type II diabetes mellitus include (but not limited to) coronary artery disease, stroke, hypertension, nephropathy, peripheral vascular disease, neurological disease and retinopathy.

Compared with the prior art, the present invention has the following main advantages:

(1) the crystal form of the present invention has a higher purity;

(2) the crystal form of the present invention has superior stability, especially thermal stability;

(3) the crystal form of the present invention has a lower hygroscopicity, and when the relative humidity RH is less than 50%, the crystal form has a hygroscopicity of less than 0.3%;

(4) the crystal form of the present invention is not easily degraded under conventional conditions;

(5) the preparation method of the crystal form of the invention is simple in operation, easy to control, and has good reproducibility, and is suitable for industrial production;

(6) the crystal form of the present invention has superior oral hypoglycemic activity;

(7) the crystal form of the present invention can improve the solubility of a compound, enhance oral absorption capacity, improve bioavailability, and is more effective in preventing or treating type II diabetes.

The present invention will be further illustrated below with reference to the specific examples. It should be understood that these examples are only to illustrate the invention but not to limit the scope of the invention. The experimental methods with no specific conditions described in the following examples are generally performed under the conventional conditions, or according to the manufacture's instructions. Unless indicated otherwise, parts and percentage are calculated by weight.

Unless otherwise defined, all professional and scientific terminology used in the text have the same meanings as known to the skilled in the art. In addition, any methods and materials similar or equal with the record content can apply to the methods of the invention. The method of the preferred embodiment described herein and the material are only for demonstration purposes.

Common Test Methods and Test Parameters

In the present invention, the crystal is subjected to a series of general tests as follows.

X-ray Diffraction (XRD) is a structural analysis method for spatial distribution of internal atoms in matter by using X-ray diffraction formed by crystals. When X-rays having a certain wavelength are irradiated onto a crystalline substance, the X-rays are scattered due to the presence of a regularly arranged atom or ion in the crystal, and the scattered X-rays are intensified in some directions to show unique diffraction phenomenon corresponding to crystalline structure.

In the present invention, the test parameters of XRD are as follows: instrument model: Bruker D8advance; target: Cu—$K_\alpha$ (40 kV, 40 mA); sample to detector distance: 30 cm; scanning range: 3°~40° (2 theta value); scanning step: 0.1 s.

Thermo Gravimetric Analysis (TGA) is an analytical technique for determining the mass change of a substance with temperature under programmed temperature control conditions. Thermo Gravimetric Analysis can be used to obtain the heat generated by the thermal changes of the sample. It is suitable for checking the loss of crystallization solvent or crystal water molecules or the sublimation and decomposition process and value of of the sample in a crystalline material. It can also effectively distinguish whether the material contains the crystallization solvent or crystalline water.

In the present invention, the test parameters of the TGA are as follows: Instrument type: Netzsch TG 209F3; Crucible: Alumina crucible; Temperature range: 30 to 400° C.; Scanning rate: 10 K/min; purge gas: 25 mL/min; Protective gas: 15 mL/min.

Differential Scanning calorimeter (DSC) is a technique for determining the change of temperature difference between the sample and the inert reference (commonly used α-$Al_2O_3$) with temperature by using programme controlling heating or cooling. DSC analysis is suitable for analysing the melt decomposition state, mixed crystal matter state, crystal transformation matter state etc. of the sample.

In the present invention, the test parameters of the DSC are as follows: Instrument type: Perkin Elmer DSC 8500; Crucible: Aluminum crucible; Scanning from 50° C. to 280° C. at a heating rate of 10° C./min under nitrogen purge.

Raman Spectroscopy (RM) is a method of studying the molecular vibration based on the Raman effects. In contrast to the infrared absorption spectrum, the Raman Spectroscopy studies the frequency of the scattered light generated by the interaction of the molecule and the light. Non-polar groups, which generally have unobvious infrared absorption, have obvious Raman spectra absorption.

In the present invention, the test parameters of the RM are as follows: Instrument type: Thermo DXR Raman Microscope (confocal microscopy Raman spectrometer); laser wavelength: 532 nm; exposure time: 1.0 sec; exposure times: 10.

Infra-red Spectrometry (IR) is the first analytical method used for the recognition and identification of crystalline substances. Due to different electrical environment of covalent bond in different crystal molecules, the covalent bond strength may change, and the change of covalent bond strength will inevitably lead to different IR spectra of different crystal forms.

In the present invention, the test parameters of IR are as follows: instrument model: Nicolet 6700 Fourier transform infrared spectrometer; single point ATR method, resolution 4.0 $cm^{-1}$.

Dynamic vapor absorption (DVS) test/water absorption test rapidly measures the increase and loss of the moisture in the sample caused by flow carrier gas with set relative humidity (RH), wherein the sample is placed on a digital microbalance with high sensitivity and high stability at a self-suspension state, and then the adsorption/desorption of water vapor is measured by measuring the increase/decrease of mass of the material, thereby determining the hygroscopicity of the sample.

In the present invention, the test parameters of the DVS are as follows: Instrument type: SMS DVS Intrinsic; Non-hydrate: 0 to 95%-0% RH; Temperature: 25° C.; Hydrate: 40 to 95%-0% RH; Temperature: 25° C.

Example 1

Preparation of Crystal Form A of (R)-methyl-2-(3-aminopiperidin-1-yl)-3-(2-cyanobenzyl)-4-carbonyl-3,4-dihydrothiophene[3,2-d]pyrimidine-6-carboxylic acid maleate (No. 1)

200 mg of (R)-methyl-2-(3-aminopiperidin-1-yl)-3-(2-cyanobenzyl)-4-carbonyl-3,4-dihydrothiophene[3,2-d]pyrimidine-6-carboxylic acid maleate was dissolved in 10 mL of ethanol, and crystals were crystallized with stirring at room temperature until no more solids were crystallized, and the crystallization time was about 2 hours. The obtained solids were filtered, placed in a vacuum drying oven, and dried under vacuum for 70 hours at 25° C., 5 KPa to obtain 110 mg of crystal form A of (R)-methyl-2-(3-aminopiperidin-1-yl)-3-(2-cyanobenzyl)-4-carbonyl-3,4-dihydrothiophene[3,2-d]pyrimidine-6-carboxylic acid maleate crystal.

Result

The crystal form A of the crystal obtained in Example 1 was subjected to tests, such as XRD, TGA, DSC, DVS, Raman and IR etc.

FIG. 1 is an XRD pattern of crystal form A of Example 1, and it can be seen from FIG. 1 that crystal form A has absorption peaks at 3.72°, 7.47°, 10.74°, 11.44°, 12.28°, 14.30°, 15.20°, 17.11°, 17.32°, 18.16°, 19.22°, 21.59°, 23.15°, 25.76°, 28.02°, 32.82°.

Figure 2:
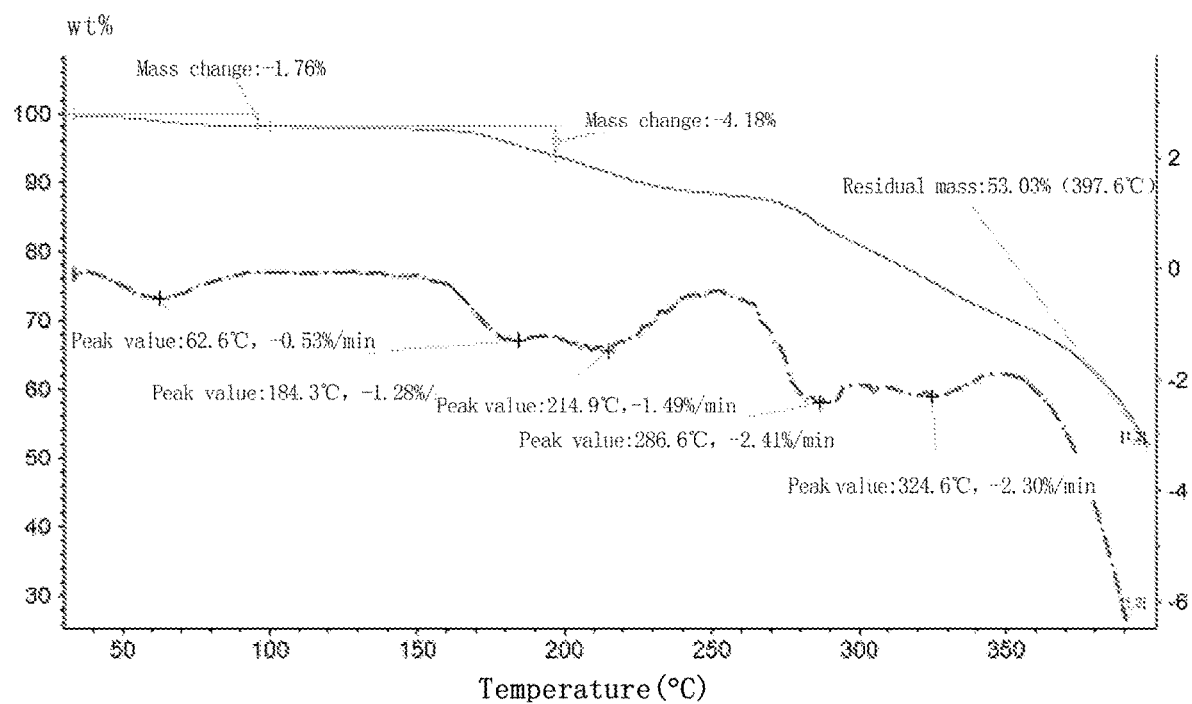
FIG. 2 is a TG diagram of the crystal form A of a crystal of Example 1 of the present invention.

FIG. 2 is a TG diagram of the crystal form A of Example 1, and it can be seen from FIG. 2 that the crystal form A has a weight loss of 47.97% at 210-400° C.

Figure 3:
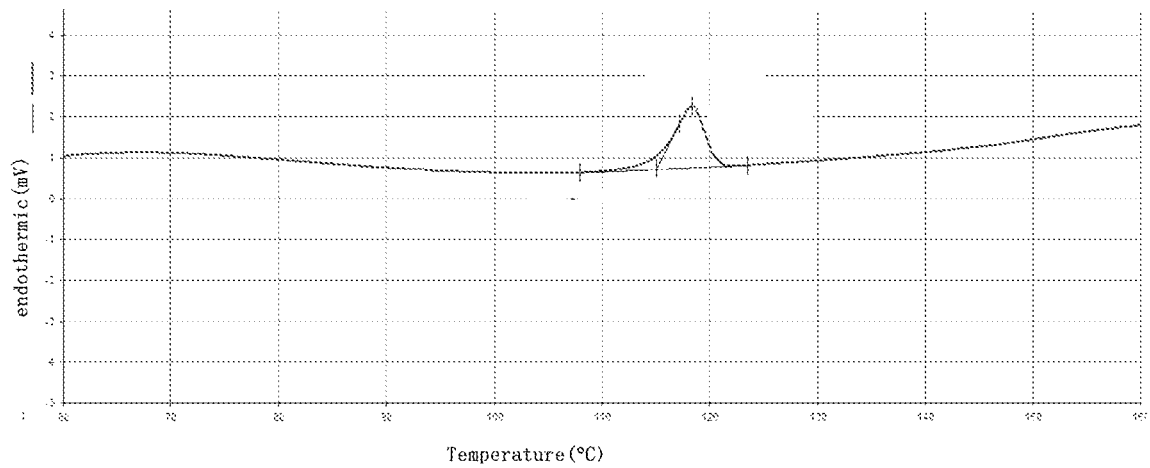
FIG. 3 is a differential scanning calorimetry (DSC) analysis spectrum of the crystal form A of a crystal of Example 1 of the present invention.

FIG. 3 is a differential scanning calorimetry (DSC) analysis spectrum of the crystal form A of Example 1, and it can be seen from FIG. 3 that the corresponding DSC of the crystal form A shows a melting point of 118.37° C.

Figure 4:
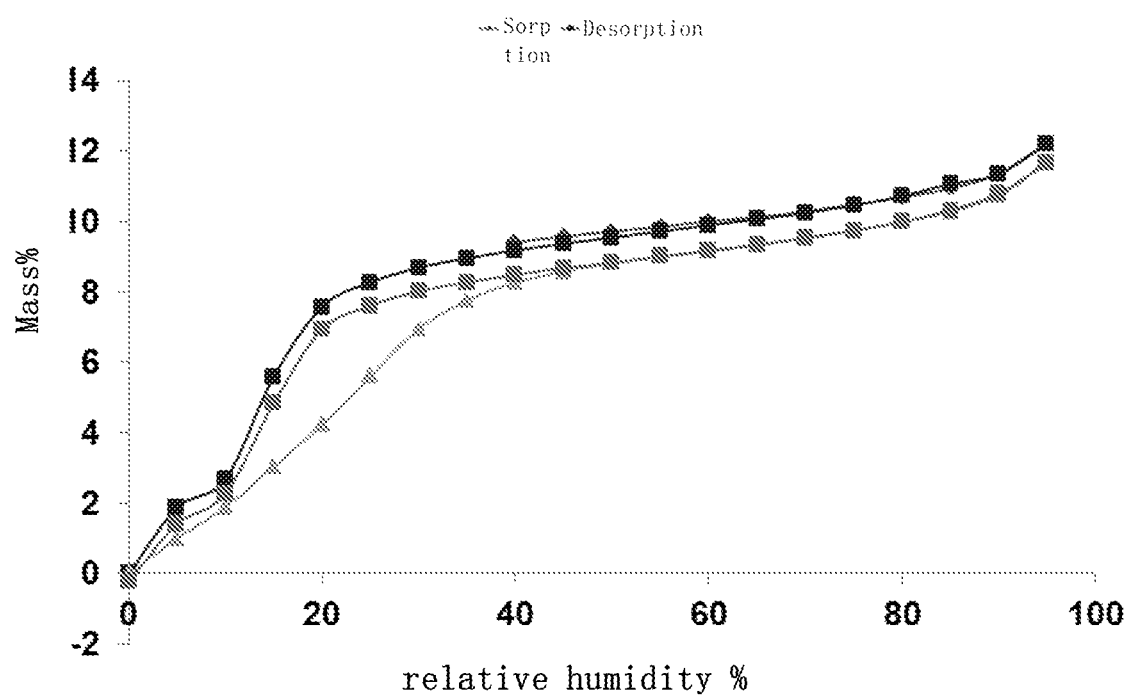
FIG. 4 is a hygroscopicity analysis (DVS) spectrum of the crystal form A of a crystal of Example 1 of the present invention.

FIG. 4 is a hygroscopicity analysis (DVS) pattern of the crystal form A of Example 1. It can be seen from FIG. 4 that the crystal from A has a slight hygroscopicity in the range of conventional storage humidity, the variation range of which is small (less than 2.0%).

Figure 5:
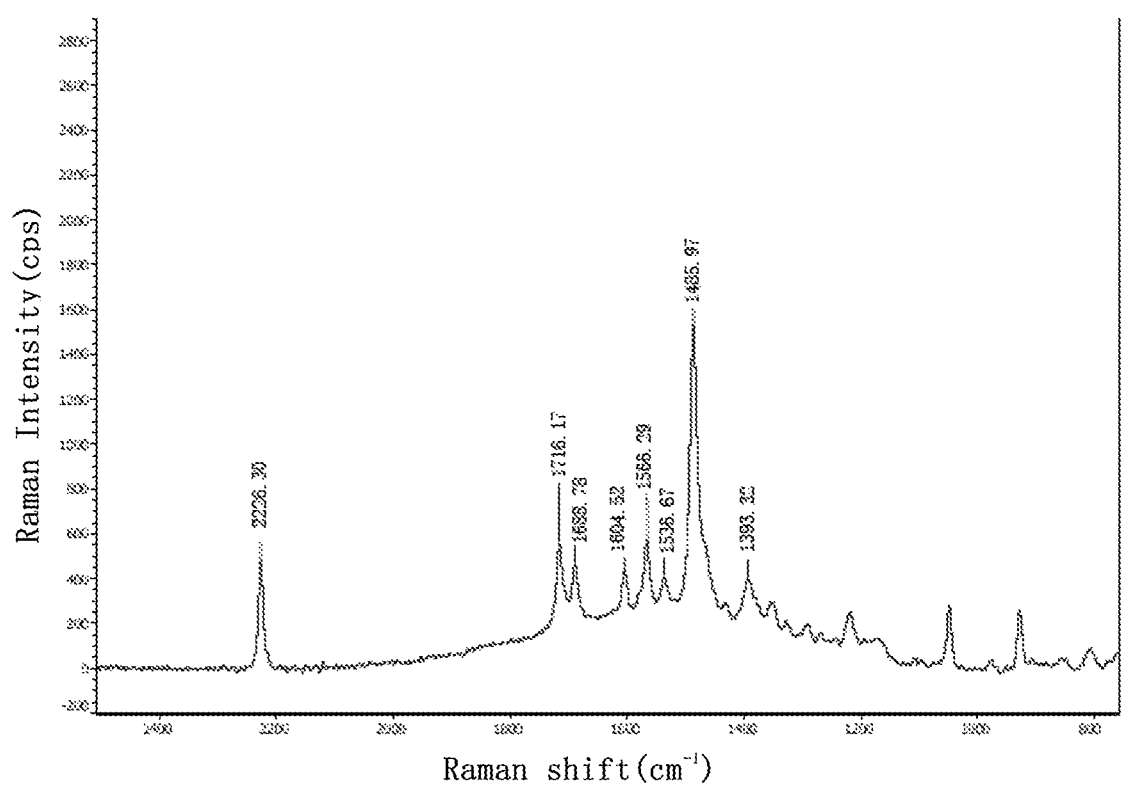
FIG. 5 is a Raman spectrum diagram of the crystal form A of a crystal of Example 1 of the present invention.

FIG. 5 is a Raman spectrum diagram of the crystal form A of Example 1, and it can be seen from FIG. 5 that the crystal form A has characteristic absorption peaks at 2226 $cm^{-1}$, 1716 $cm^{-1}$, 1689 $cm^{-1}$, 1604 $cm^{-1}$, 1566 $cm^{-1}$, 1536 $cm^{-1}$, 1486 $cm^{-1}$, 1393 $cm^{-1}$.

Figure 6:
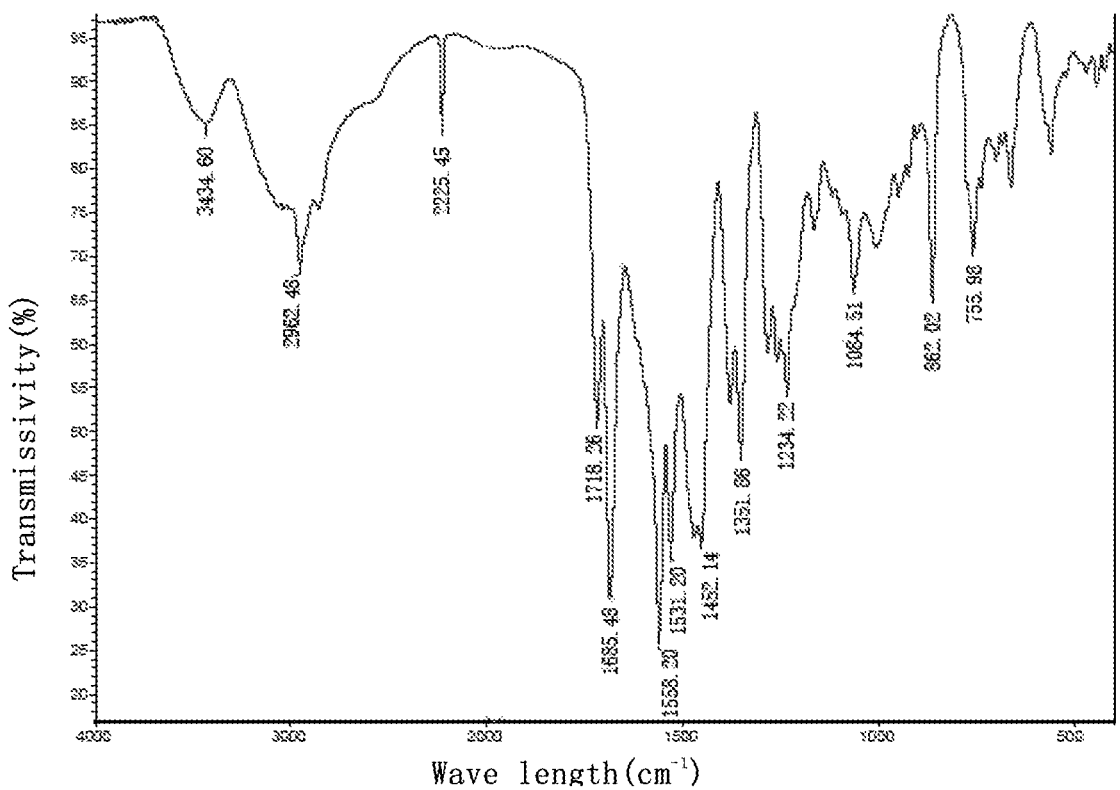
FIG. 6 is an infrared spectrum (IR) pattern of the crystal form A of a crystal of Example 1 of the present invention.

FIG. 6 is an infrared spectrum (IR) diagram of the crystal form A of Example 1, and it can be seen from FIG. 6 that the crystal form A has characteristic absorption peaks at 3435 $cm^{-1}$, 2952 $cm^{-1}$, 2225 $cm^{-1}$, 1718 $cm^{-1}$, 1685 $cm^{-1}$, 1558 $cm^{-1}$, 1531 $cm^{-1}$, 1452 $cm^{-1}$, 1234 $cm^{-1}$, 1064 $cm^{-1}$, 862 $cm^{-1}$, 756 $cm^{-1}$.

Example 2

Preparation of Crystal Form A of (R)-methyl-2-(3-aminopiperidin-1-yl)-3-(2-cyanobenzyl)-4-carbonyl-3,4-dihydrothiophene[3,2-d]pyrimidine-6-carboxylic acid maleate (No. 2)

200 mg of (R)-methyl-2-(3-aminopiperidin-1-yl)-3-(2-cyanobenzyl)-4-carbonyl-3,4-dihydrothiophene[3,2-d]pyrimidine-6-carboxylic acid was dissolved in 10 mL of water, and crystals were crystallized with stirring at room temperature until no more solids were crystallized. The obtained solids were filtered, placed in a vacuum drying oven and vacuum dried for 70 hours at 25° C. under 5 KPa to give 100 mg of crystal form A of (R)-methyl-2-(3-aminopiperidin-1-yl)-3-(2-cyanobenzyl)-4-carbonyl-3,4-dihydrothiophene[3,2-d]pyrimidine-6-carboxylic acid maleate.

The XRD result of the obtained product was essentially the same as that of Example 1.

Example 3

Preparation of Crystal Form A of (R)-methyl-2-(3-aminopiperidin-1-yl)-3-(2-cyanobenzyl)-4-carbonyl-3,4-dihydrothiophene[3,2-d]pyrimidine-6-carboxylic acid maleate (No. 3)

200 mg of (R)-methyl-2-(3-aminopiperidin-1-yl)-3-(2-cyanobenzyl)-4-carbonyl-3,4-dihydrothiophene[3,2-d]pyrimidine-6-carboxylic acid was dissolved in 10 mL of methanol, and crystals were crystallized with stirring at room temperature until no more solid was crystallized. The obtained solids were filtered, placed in a vacuum drying oven and vacuum dried for 70 hours at 25° C. under 5 KPa to give 100 mg of crystal form A of (R)-methyl-2-(3-aminopiperidin-1-yl)-3-(2-cyanobenzyl)-4-carbonyl-3,4-dihydrothiophene[3,2-d] pyrimidine-6-carboxylic acid maleate.

The XRD result of the obtained product was essentially the same as that of Example 1.

Example 4

Preparation of Crystal Form B of (R)-methyl-2-(3-aminopiperidin-1-yl)-3-(2-cyanobenzyl)-4-carbonyl-3,4-dihydrothiophene[3,2-d]pyrimidine-6-carboxylic acid maleate (No. 4)

200 mg of (R)-methyl-2-(3-aminopiperidin-1-yl)-3-(2-cyanobenzyl)-4-carbonyl-3,4-dihydrothiophene[3,2-d]pyrimidine-6-carboxylic acid maleate was dissolved in 10 mL of ethyl acetate, and crystals were crystallized with stirring at room temperature until no more solids were crystallized, and the crystallization time was about 2 hours. The obtained solids were filtered, placed in a vacuum drying oven, and dried under vacuum for 70 hours at 25° C., 5 KPa to obtain 110 mg of crystal B of (R)-methyl-2-(3-aminopiperidin-1-yl)-3-(2-cyanobenzyl)-4-carbonyl-3,4-dihydrothiophene[3,2-d]pyrimidine-6-carboxylic acid maleate.

Result

The crystal form B of the crystal obtained in Example 4 was subjected to tests, such as XRD, TGA, DSC, DVS, Raman and IR etc.

FIG. 7 is an XRD pattern of the crystal form B of Example 4, and it can be seen from FIG. 7 that the crystal form B has absorption peaks at 5.37°, 7.85°, 11.20°, 12.01°, 14.93°, 16.04°, 20.09°, 22.10°, 22.61°, 24.19°, 30.16°, 32.12°, 32.39°.

Figure 8:
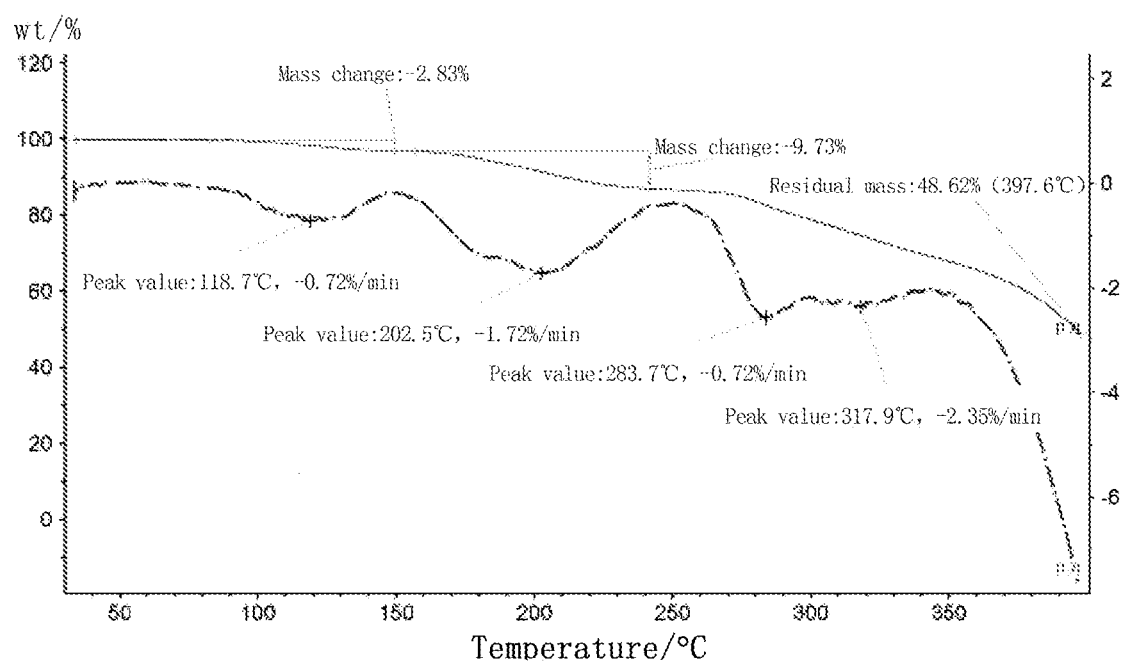
FIG. 8 is a TG diagram of the crystal form B of a crystal of Example 4 of the present invention.

FIG. 8 is a TG diagram of the crystal form B of Example 4, and it can be seen from FIG. 8 that the crystal form B has a weight loss of 51.38% at 210-400° C.

Figure 9:
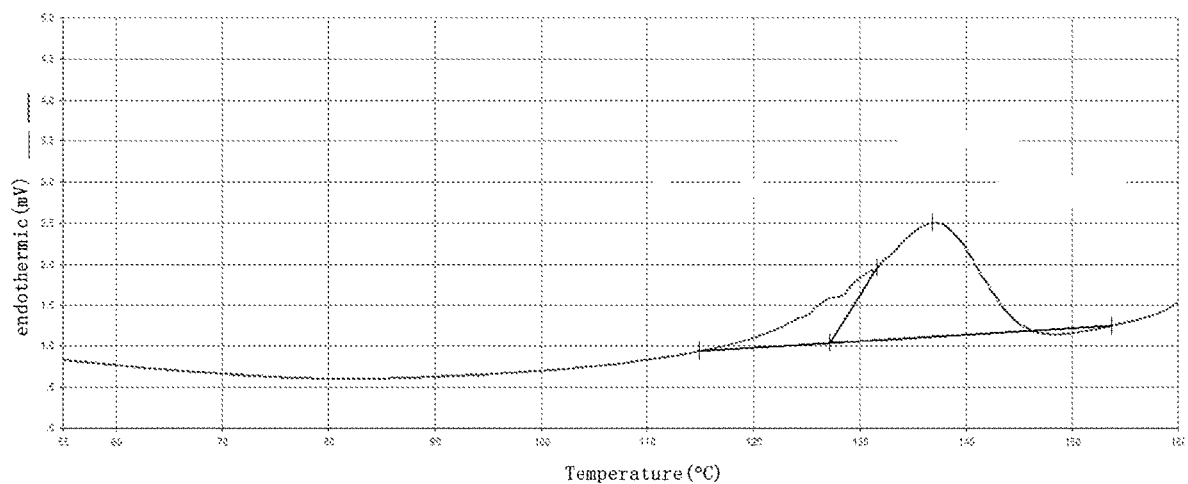
FIG. 9 is a differential scanning calorimetry (DSC) analysis spectrum of the crystal form B of a crystal of Example 4 of the present invention.

FIG. 9 is a differential scanning calorimetry (DSC) analysis spectrum of the crystal form B of Example 4. It can be seen from FIG. 9 that the corresponding DSC of the crystal form B shows a melting point of 136.77° C.

Figure 10:
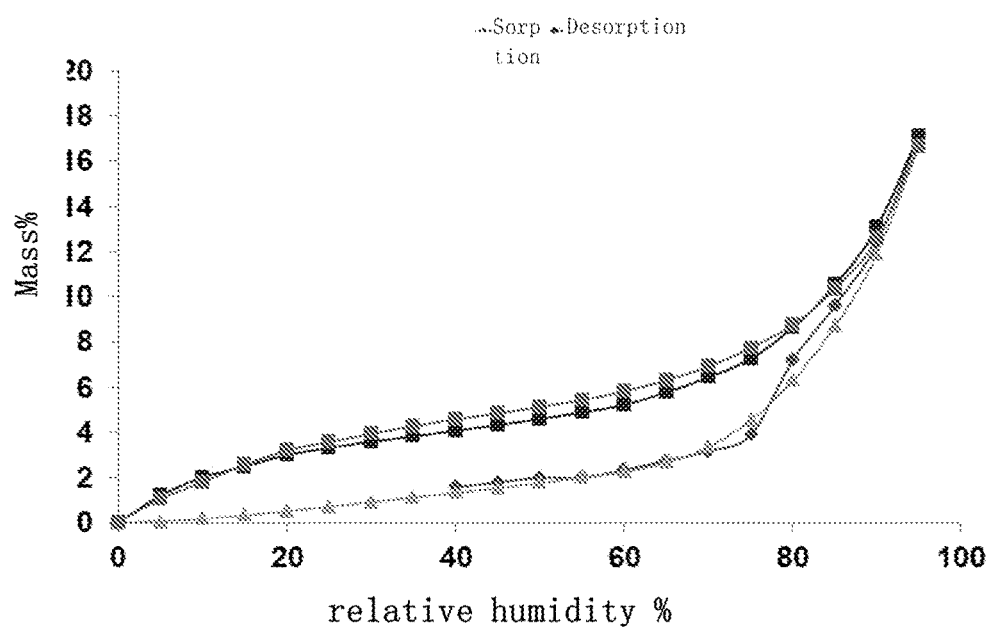
FIG. 10 is a hygroscopicity analysis (DVS) spectrum of the crystal form B of a crystal of Example 4 of the present invention.

FIG. 10 is a hygroscopicity analysis (DVS) pattern of the crystal form B of Example 4. It can be seen from FIG. 10 that the crystal from B has a slight hygroscopicity in the range of conventional storage humidity, the variation range of which is small (less than 2.0%).

Figure 11:
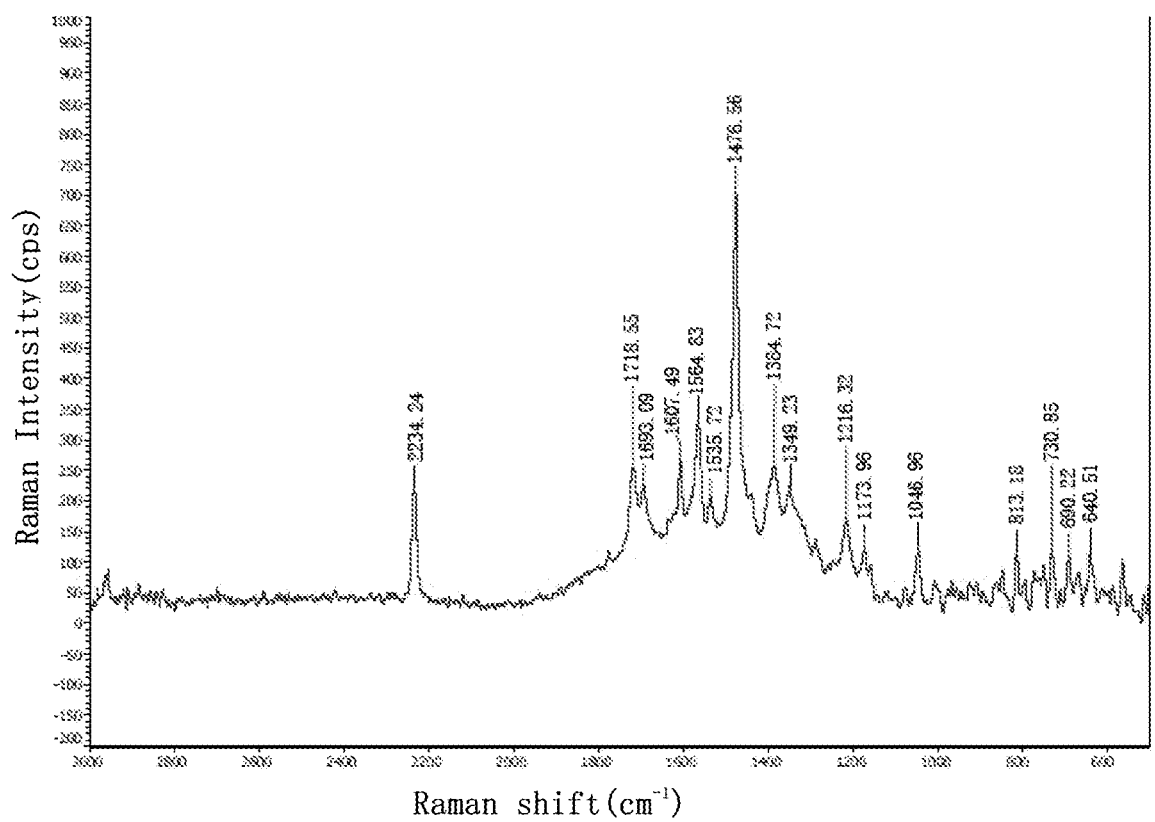
FIG. 11 is a Raman spectrum of the crystal form B of a crystal of Example 4 of the present invention.

FIG. 11 is a Raman spectrum of the crystal form B of Example 4, and it can be seen from FIG. 11 that the crystal form B has characteristic absorption peaks at 2234 $cm^{-1}$, 1718 $cm^{-1}$, 1693 $cm^{-1}$, 1607 $cm^{-1}$, 1565 $cm^{-1}$, 1536 $cm^{-1}$, 1476 $cm^{-1}$, 1386 $cm^{-1}$, 1349 $cm^{-1}$, 1216 $cm^{-1}$, 1174 $cm^{-1}$, 1047 $cm^{-1}$, 813 $cm^{-1}$, 730 $cm^{-1}$, 690 $cm^{-1}$, 641 $cm^{-1}$.

Figure 12:
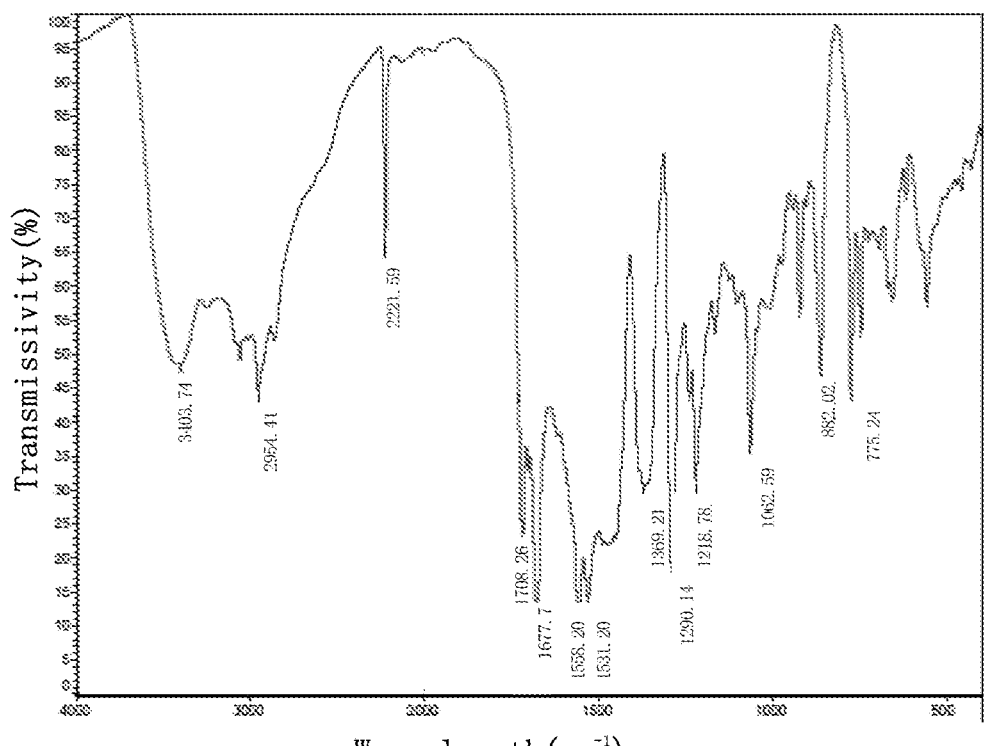
FIG. 12 is an infrared spectrum (IR) pattern of the crystal form B of a crystal of Example 4 of the present invention.

FIG. 12 is an infrared spectrum (IR) of the crystal form B of Example 1, and it can be seen from FIG. 12 that the crystal form B has characteristic absorption peaks at 3404 $cm^{-1}$, 2954 $cm^{-1}$, 2222 $cm^{-1}$, 1718 $cm^{-1}$, 1678 $cm^{-1}$, 1558 $cm^{-1}$, 1531 $cm^{-1}$, 1369 $cm^{-1}$, 1290 $cm^{-1}$, 1219 $cm^{-1}$, 1063 $cm^{-1}$, 862 $cm^{-1}$, 775 $cm^{-1}$.

Example 5

Preparation of Crystal Form B of (R)-methyl-2-(3-aminopiperidin-1-yl)-3-(2-cyanobenzyl)-4-carbonyl-3,4-dihydrothiophene[3,2-d]pyrimidine-6-carboxylic acid maleate (No. 5)

200 mg of (R)-methyl-2-(3-aminopiperidin-1-yl)-3-(2-cyanobenzyl)-4-carbonyl-3,4-dihydrothiophene[3,2-d]pyrimidine-6-carboxylic acid was dissolved in 10 mL of toluene, and crystals were crystallized with stirring at room temperature until no more solids were crystallized. The obtained solids were filtered, placed in a vacuum drying oven and vacuum dried for 70 hours at 25° C. under 5 KPa to give 120 mg of crystal form B of (R)-methyl-2-(3-aminopiperidin-1-yl)-3-(2-cyanobenzyl)-4-carbonyl-3,4-dihydrothiophene[3,2-d] pyrimidine-6-carboxylic acid maleate.

The XRD result of the obtained product was essentially the same as that of Example 4.

Example 6

Preparation of Crystal Form B of (R)-methyl-2-(3-aminopiperidin-1-yl)-3-(2-cyanobenzyl)-4-carbonyl-3,4-dihydrothiophene[3,2-d]pyrimidine-6-carboxylic acid maleate (No. 6)

200 mg of (R)-methyl-2-(3-aminopiperidin-1-yl)-3-(2-cyanobenzyl)-4-carbonyl-3,4-dihydrothiophene[3,2-d]pyrimidine-6-carboxylic acid was dissolved in 10 mL of methyl tert-butyl ether, and crystals were crystallized with stirring at room temperature until no more solids were crystallized. The obtained solids were filtered, placed in a vacuum drying oven and vacuum dried for 70 hours at 25° C. under 5 KPa to give 100 mg of crystal form B of (R)-methyl-2-(3-aminopiperidin-1-yl)-3-(2-cyanobenzyl)-4-carbonyl-3,4-dihydrothiophene[3,2-d] pyrimidine-6-carboxylic acid maleate.

The XRD result of the obtained product was essentially the same as that of Example 4.

Example 7

Preparation of Crystal Form C of (R)-methyl-2-(3-aminopiperidin-1-yl)-3-(2-cyanobenzyl)-4-carbonyl-3,4-dihydrothiophene[3,2-d]pyrimidine-6-carboxylic acid maleate (No. 7)

200 mg of (R)-methyl-2-(3-aminopiperidin-1-yl)-3-(2-cyanobenzyl)-4-carbonyl-3,4-dihydrothiophene[3,2-d]pyrimidine-6-carboxylic acid maleate was dissolved in 10 mL of acetonitrile, 12 mL of n-hexane was added, and crystals were crystallized with stirring at room temperature until no more solids were crystallized, and the crystallization time was about 2 hours. The obtained solids were filtered, placed in a vacuum drying oven and dried under vacuum for 70 hours at 25° C., 5 KPa to obtain 110 mg of crystal C of (R)-methyl-2-(3-aminopiperidin-1-yl)-3-(2-cyanobenzyl)-4-carbonyl-3,4-dihydrothiophene[3,2-d]pyrimidine-6-carboxylic acid maleate.

Result

The crystal form C of the crystal obtained in Example 7 was subjected to tests, such as XRD, TGA, DSC, DVS, Raman and IR etc.

FIG. 13 is an XRD pattern of the crystal form C of Example 7, and it can be seen from FIG. 13 that the crystal form C has absorption peaks at 6.63°, 8.67°, 11.16°, 11.64°, 15.24°, 16.43°, 17.06°, 17.41°, 18.00°, 18.61°, 18.90°, 19.46°, 19.96°, 20.84°, 21.35±0.2°, 22.81±0.2°, 23.11±0.2°, 23.59±0.2°, 24.7°, 25.18°, 25.74°, 27.62 Å, 28.32°, 31.17°.

Figure 14:
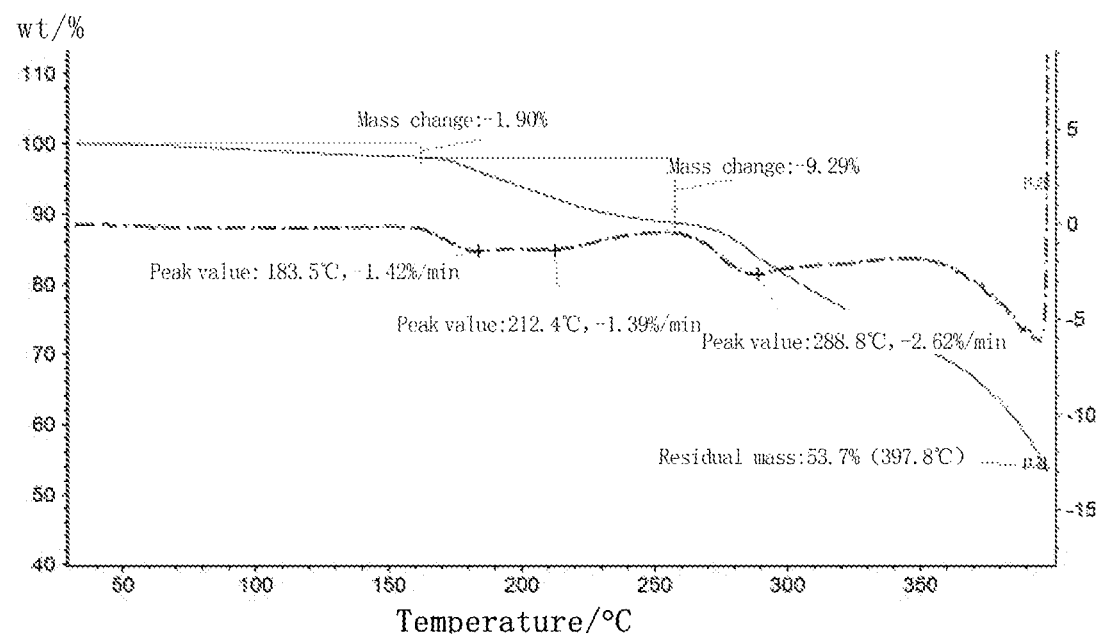
FIG. 14 is a TG diagram of the crystal form C of a crystal of Example 7 of the present invention.

FIG. 14 is a TG diagram of the crystal form C of Example 7, and it can be seen from FIG. 14 that the crystal form C has a weight loss of 46.30% at 210-400° C.

Figure 15:
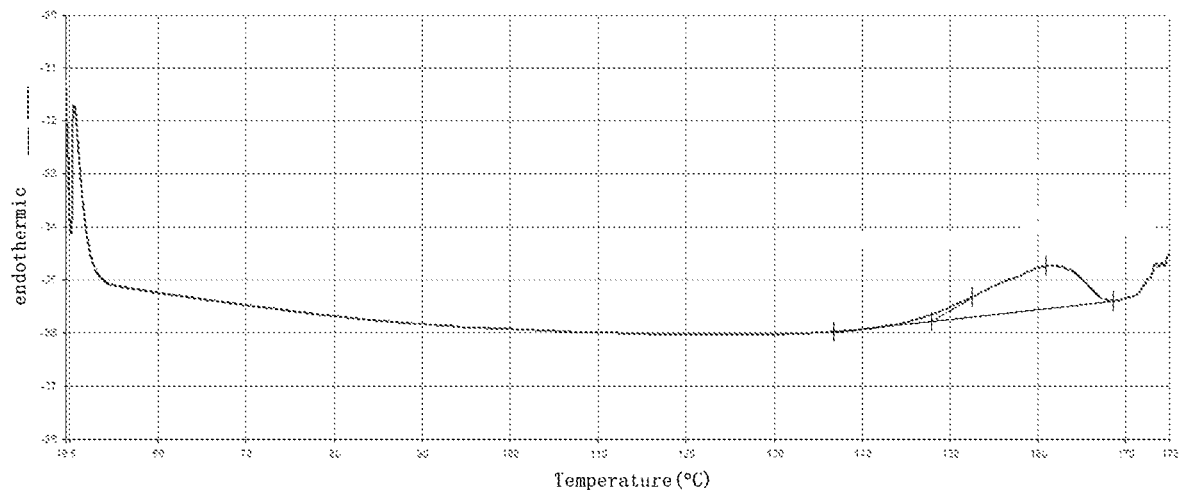
FIG. 15 is a differential scanning calorimetry (DSC) analysis spectrum of the crystal form C of a crystal of Example 7 of the present invention.

FIG. 15 is a differential scanning calorimetry (DSC) analysis spectrum of the crystal form C of Example 7, and it can be seen from FIG. 15 that the corresponding DSC of the crystal form A shows a melting point of 160.90° C.

Figure 16:
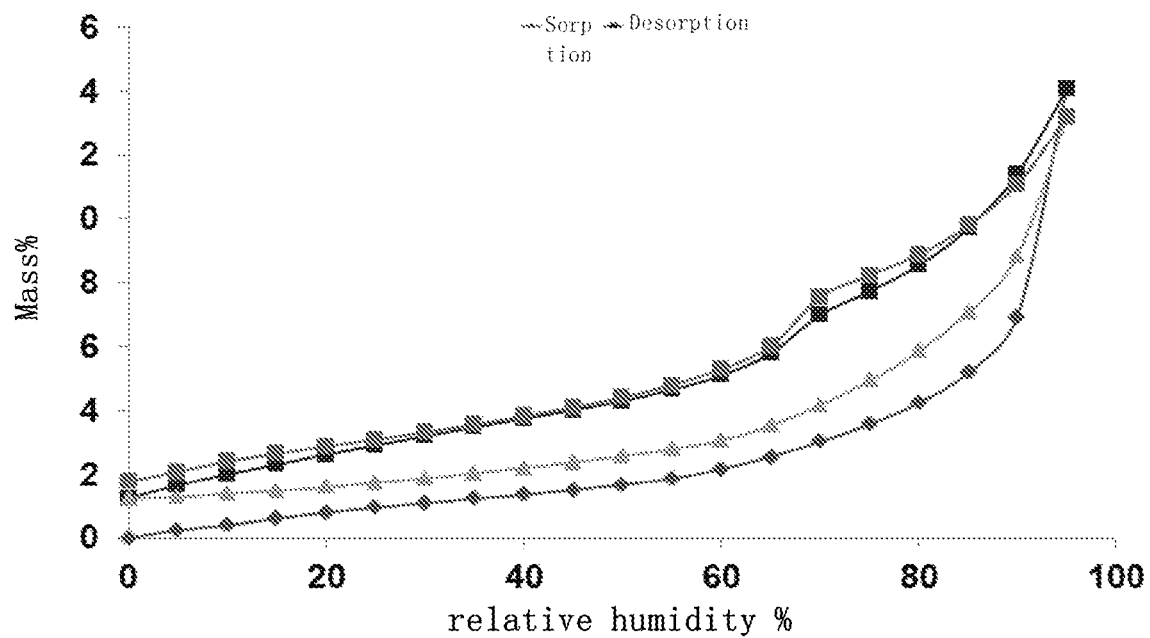
FIG. 16 is a hygroscopicity analysis (DVS) spectrum of the crystal form C of a crystal of Example 7 of the present invention.

FIG. 16 is a hygroscopicity analysis (DVS) pattern of the crystal form C of Example 7. It can be seen from FIG. 16 that the crystal from C has a slight hygroscopicity in the range of conventional storage humidity, the variation range of which is small (less than 2.0%).

Figure 17:
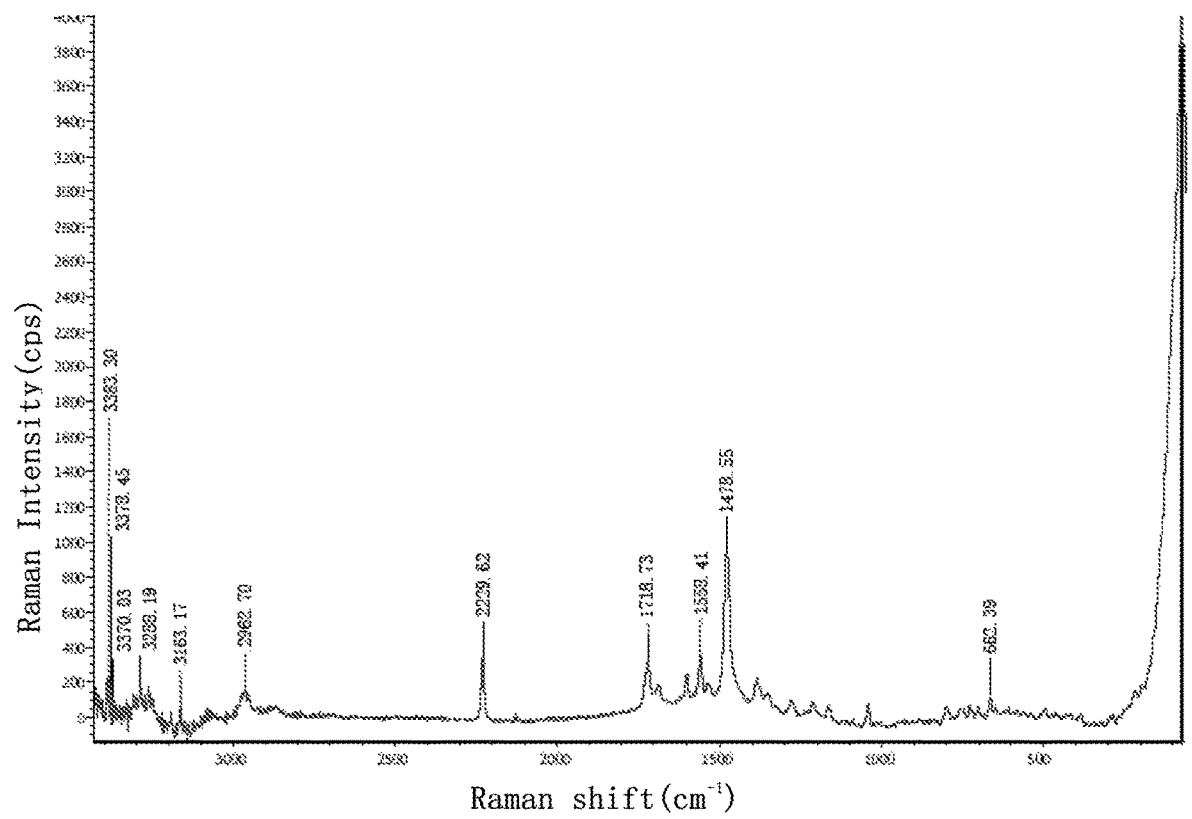
FIG. 17 is a Raman spectrum of the crystal form C of a crystal of Example 7 of the present invention.

FIG. 17 is a Raman spectrum diagram of the crystal form C of Example 7, and it can be seen from FIG. 17 that the crystal form C has characteristic absorption peaks at 3383 $cm^{-1}$, 3378 $cm^{-1}$, 3370 $cm^{-1}$, 3288 $cm^{-1}$, 3163 $cm^{-1}$, 2963 $cm^{-1}$, 2230 $cm^{-1}$, 1719 $cm^{-1}$, 1558 $cm^{-1}$, 1478 $cm^{-1}$, 662 $cm^{-1}$.

Figure 18:
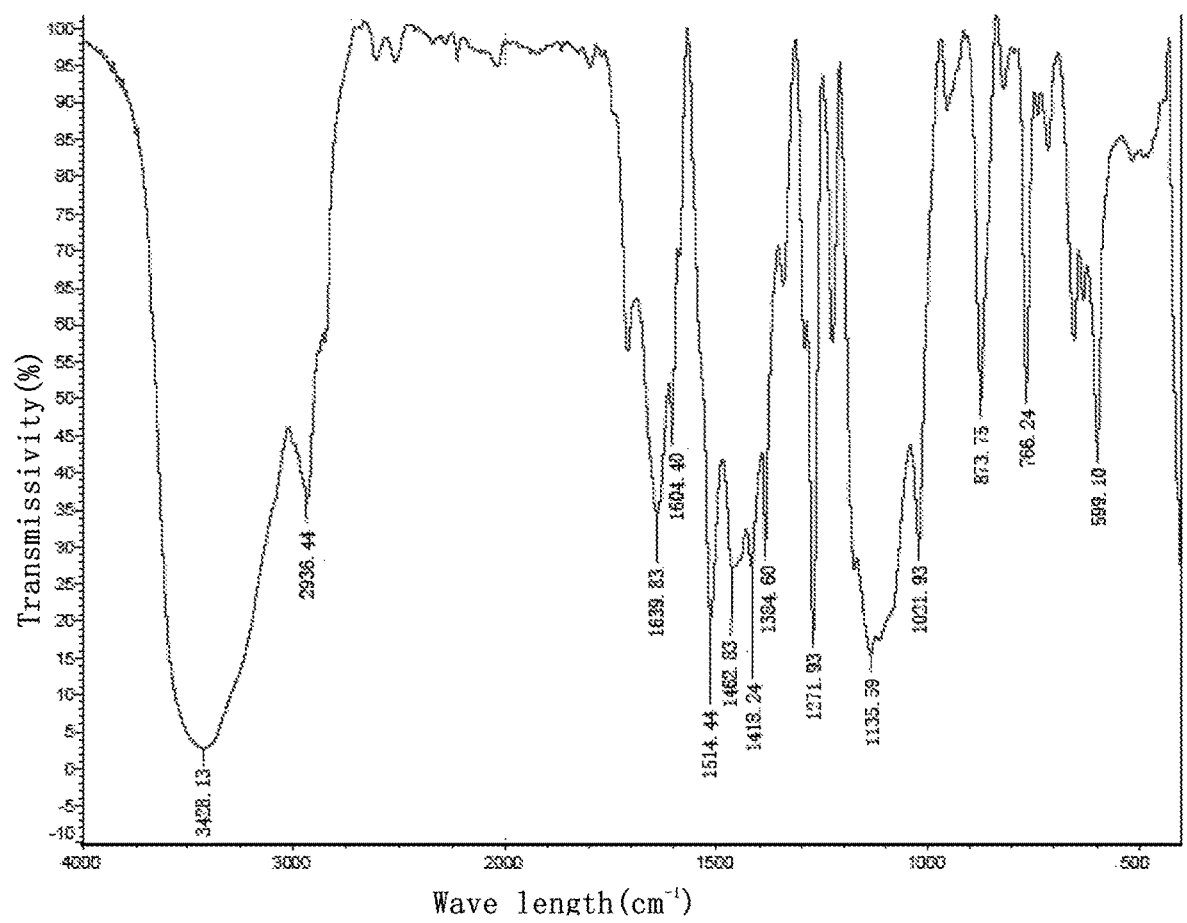
FIG. 18 is an infrared spectrum (IR) pattern of the crystal form C of a crystal of Example 7 of the present invention.

FIG. 18 is an infrared spectrum (IR) of the crystal form C of Example 7, and it can be seen from FIG. 18 that the crystal form C has characteristic absorption peaks at 3428 $cm^{-1}$, 2936 $cm^{-1}$, 1640 $cm^{-1}$, 1514 $cm^{-1}$, 1463 $cm^{-1}$, 1418 $cm^{-1}$, 1385 $cm^{-1}$, 1272 $cm^{-1}$, 1136 $cm^{-1}$, 1022 $cm^{-1}$, 874 $cm^{-1}$, 766 $cm^{-1}$, 599 $cm^{-1}$.

All literatures mentioned in the present invention are incorporated by reference herein, as though individually incorporated by reference. Additionally, it should be understood that after reading the above teaching, many variations and modifications may be made by the skilled in the art, and these equivalents also fall within the scope as defined by the appended claims.

The invention claimed is:

1. A crystal form of a compound of formula I, wherein the crystal form is a crystal having high stability and low hygroscopicity, and the crystal form is selected from the group consisting of crystal form A, crystal form B and crystal form C

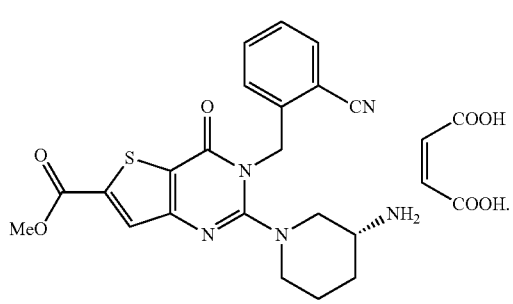

I

2. The crystal form of claim 1, wherein the "low hygroscopicity" means that the weight gain of crystal form A, crystal form B or crystal form C is calculated to be ≤1%, after being placed in a desiccator for 24 hours at a temperature of 80° C. and a humidity of 80% and taken out.

3. The crystal form of claim 1, wherein the crystal form A has one or more characteristics selected from the group consisting of:

(1) the X-ray powder diffraction pattern of the crystal form A includes 3 or more 2θ values selected from the group consisting of 3.72±0.2°, 7.47±0.2°, 11.44±0.2°, 12.28±0.2°, 21.59±0.2°; and/or (2) the differential scanning calorimetry analysis spectrum (DSC spectrum) of the crystal form A has a characteristic peak within the range of 118±5° C.; and/or (3) the thermogravimetric analysis pattern of the crystal form A includes 3 or more characteristic absorption peaks selected from the group consisting of 63±5° C., 184±5° C., 215±5° C., 287±5° C., 325±5° C.; and/or (4) the thermal weight loss of the crystal form A is 47-48 wt % at 400° C.; and/or (5) the starting value of the endothermic transition temperature of the crystal form A is 115±2° C.; and/or (6) the Raman spectrum of the crystal form A includes the following characteristic absorption peaks expressed by the wavelength λ: 2226±2 1716±2 $cm^{-1}$, 1689±2 $cm^{-1}$, 1604±2 $cm^{-1}$, 1566±2 $cm^{-1}$, 1536±2 $cm^{-1}$, 1486±2 $cm^{-1}$, 1393±2 $cm^{-1}$; and/or (7) the IR pattern of the crystal form A includes the following characteristic absorption peaks expressed by the wavelength λ: 3435±2 2952±2 $cm^{-1}$, 2225±2 $cm^{-1}$, 1718±2 $cm^{-1}$, 1685±2 $cm^{-1}$, 1558±2 $cm^{-1}$, 1531±2 $cm^{-1}$, 1452±2 $cm^{-1}$, 1234±2 $cm^{-1}$, 1064±2 $cm^{-1}$, 862±2 $cm^{-1}$, 756±2 $cm^{-1}$.

4. The crystal form of claim 1, wherein the crystal form B has one or more characteristics selected from the group consisting of:

(1) the X-ray powder diffraction pattern of the crystal form B includes 3 or more 2θ values selected from the group consisting of: 5.37±0.2°, 12.01±0.2°, 14.93±0.2°, 16.04±0.2°, 20.09±0.2°; and/or (2) the differential scanning calorimetry analysis spectrum (DSC spectrum) of the crystal form B has a characteristic peak within the range of 137±5° C.; and/or (3) the starting value of the endothermic transition temperature of the crystal form B is 127±2° C.; and/or (4) the thermogravimetric analysis pattern of the crystal form B includes 3 or more characteristic absorption peaks selected from the group consisting of: 119±5° C., 202±5° C., 284±5° C., 318±5° C.; and/or (5) the thermal weight loss of the crystal form B is 51-52 wt % at 400° C.; and/or (6) the Raman spectrum of the crystal form B includes the following characteristic absorption peaks expressed by the wavelength λ: 2234±2 1718±2 $cm^{-1}$, 1693±2 $cm^{-1}$, 1607±2 $cm^{-1}$, 1565±2 $cm^{-1}$, 1536±2 $cm^{-1}$, 1476±2 $cm^{-1}$, 1386±2 $cm^{-1}$, 1349±2 $cm^{-1}$, 1216±2 $cm^{-1}$, 1174±2 $cm^{-1}$, 1047±2 $cm^{-1}$, 813±2 730±2 $cm^{-1}$, 690±2 $cm^{-1}$, 641±2 $cm^{-1}$; and/or (7) the IR pattern of the crystal form B includes the following characteristic absorption peaks expressed by the wavelength λ: 3404±2 2954±2 $cm^{-1}$, 2222±2 $cm^{-1}$, 1718±2 $cm^{-1}$, 1678±2 $cm^{-1}$, 1558±2 $cm^{-1}$, 1531±2 $cm^{-1}$, 1369±2 $cm^{-1}$, 1290±2 $cm^{-1}$, 1219±2 $cm^{-1}$, 1063±2 $cm^{-1}$, 862±2 $cm^{-1}$, 775±2 $cm^{-1}$.

5. The crystal form of claim 1, wherein the crystal form C has one or more characteristics selected from the group consisting of:

(1) the X-ray powder diffraction pattern of the crystal form C includes 3 or more 2θ values selected from the group consisting of: 6.63±0.2°, 11.16±0.2°, 17.06±0.2°, 19.46±0.2°, 20.84±0.2°, 25.74±0.2°; and/or (2) the differential scanning calorimetry analysis spectrum (DSC spectrum) of the crystal form C has a characteristic peak within the range of 161±5° C.; and/or (3) the starting value of the endothermic transition temperature of the crystal form C is 147±2° C.; and/or (4) the thermogravimetric analysis pattern of the crystal form C comprises a characteristic absorption peak selected from the group consisting of: 183±5° C., 212±5° C., 289±5°; and/or (5) the thermal weight loss of the crystal form C is 46-47 wt % at 400° C.; and/or (6) the Raman spectrum of the crystal form C includes the following characteristic absorption peaks expressed by the wavelength λ: 3383±2 $cm^{-1}$, 3378±2 $cm^{-1}$, 3370±2 $cm^{-1}$, 3288±2 $cm^{-1}$, 3163±2 $cm^{-1}$, 2963±2 $cm^{-1}$, 2230±2 $cm^{-1}$, 1719±2 $cm^{-1}$, 1558±2 $cm^{-1}$, 1478±2 $cm^{-1}$, 662±2 $cm^{-1}$; and/or (7) the IR pattern of the crystal form C includes the following characteristic absorption peaks expressed by the wavelength λ: 3428±2 $cm^{-1}$, 2936±2 $cm^{-1}$, 1640±2 $cm^{-1}$, 1514±2 $cm^{-1}$, 1463±2 $cm^{-1}$, 1418±2 $cm^{-1}$, 1385±2 $cm^{-1}$, 1272±2 $cm^{-1}$, 1136±2 $cm^{-1}$, 1022±2 $cm^{-1}$, 874±2 $cm^{-1}$, 766±2 $cm^{-1}$, 599±2 $cm^{-1}$.

6. A method for preparing the crystal form A of claim 1, comprising the steps of:

(1) providing a first solution comprising a first solvent and a compound of formula I, the weight to volume ratio of the compound of formula I to the first solvent is from 0.1 g/L to 100 g/L, and;

(2) mixing a second solvent with the first solution, and crystallizing at 0 to 50° C. to obtain crystal form A.

7. A method for preparing the crystal form B or the crystal form C of claim 1, comprising the steps of:

(1) providing a first solution comprising a first solvent and a compound of formula I, the weight to volume ratio of the compound of formula I to the first solvent is from 0.1 g/L to 100 g/L, and;

(2) mixing a second solvent with the first solution, and crystallizing at 5 to 80° C. to obtain crystal form B or crystal form C.

8. A pharmaceutical composition, comprising:
(a) the crystal form A, B or C of claim 1, and
(b) a pharmaceutically acceptable carrier.

9. A method for treating type II diabetes and/or complications of type II diabetes in a patient, comprising administering to the patient a therapeutically effective amount of the crystal form of claim 1.

10. A method for treating type II diabetes and/or complications of type II diabetes in a patient, comprising administering to the patient a therapeutically effective amount of the pharmaceutical composition of claim 8.

11. The method of claim 6, wherein the weight to volume ratio of the compound of formula I to the first solvent is from 1 g/L to 90 g/L.

12. The method of claim 6, wherein the weight to volume ratio of the compound of formula I to the first solvent is from 10 g/L to 60 g/L.

13. The method of claim 6, wherein the weight to volume ratio of the compound of formula I to the first solvent is from 15 g/L to 40 g/L.

14. The method of claim 7, wherein the weight to volume ratio of the compound of formula I to the first solvent is from 1 g/L to 100 g/L.

15. The method of claim 7, wherein the weight to volume ratio of the compound of formula I to the first solvent is from 10 g/L to 100 g/L.

16. The method of claim 7, wherein the weight to volume ratio of the compound of formula I to the first solvent is from 50 g/L to 100 g/L.

17. A method for treating type II diabetes and/or complications of type II diabetes in a patient, comprising administering to the patient a therapeutically effective amount of the crystal form A of claim 3.

18. A method for treating type II diabetes and/or complications of type II diabetes in a patient, comprising administering to the patient a therapeutically effective amount of the crystal form B of claim 4.

19. A method for treating type II diabetes and/or complications of type II diabetes in a patient, comprising administering to the patient a therapeutically effective amount of the crystal form C of claim 5.

* * * * *